United States Patent
Taber et al.

(10) Patent No.: US 11,234,688 B2
(45) Date of Patent: Feb. 1, 2022

(54) COMPRESSION AND TENSION INSTRUMENTS AND METHODS OF USE TO REINFORCE LIGAMENTS

(71) Applicant: Crossroads Extremity Systems, LLC, Memphis, TN (US)

(72) Inventors: Justin Taber, Honolulu, HI (US); T. Wade Fallin, Hyde Park, UT (US); Phinit Phisitkul, Coralville, IA (US)

(73) Assignee: Crossroads Extremity Systems, LLC, Memphis, TN (US)

( * ) Notice: Subject to any disclaimer, the term of this patent is extended or adjusted under 35 U.S.C. 154(b) by 324 days.

(21) Appl. No.: 16/545,444

(22) Filed: Aug. 20, 2019

(65) Prior Publication Data

US 2019/0380696 A1     Dec. 19, 2019

Related U.S. Application Data

(63) Continuation of application No. 15/642,053, filed on Jul. 5, 2017, now Pat. No. 10,426,460.
(Continued)

(51) Int. Cl.
*A61B 17/58*        (2006.01)
*A61B 17/60*        (2006.01)
(Continued)

(52) U.S. Cl.
CPC ...... *A61B 17/0401* (2013.01); *A61B 17/0485* (2013.01); *A61B 17/06166* (2013.01);
(Continued)

(58) Field of Classification Search
CPC combination set(s) only.
See application file for complete search history.

(56) References Cited

U.S. PATENT DOCUMENTS

| 2,181,746 A | 11/1939 | Siebrandt |
| 2,291,413 A | 7/1942 | Siebrandt |

(Continued)

FOREIGN PATENT DOCUMENTS

| CA | 551446 A | 1/1958 |
| EP | 132284 A1 | 1/1985 |

(Continued)

OTHER PUBLICATIONS

Akros Fibulink, Akros Medical, 2017, www.akrosmedical.com, 3 pp.
(Continued)

*Primary Examiner* — Sameh R Boles
(74) *Attorney, Agent, or Firm* — David Meibos; Maywood IP Law

(57) ABSTRACT

The disclosure provides apparatus and methods of use pertaining to syndesmosis reinforcement. Embodiments include a clamp having two jaws that extend toward each other to clamp two bone portions therebetween. The clamp may include an angle gauge and an adjustment mechanism having a force gauge that combine to enable the compression of the two bone portions in an optimal direction or angle and at an optimal, measurable compression force. Embodiments also include a tension instrument configured to knotlessly lock a flexible strand construct between two anchors at the same optimal direction and tension applied by the clamp. Further embodiments include an exemplary syndesmosis reinforcement procedure that employs the clamp and the tension instrument to construct a ligament reinforcement construct that achieves optimal anatomic positioning in both directional alignment and the reduction force applied by the construct. Other embodiments are disclosed.

12 Claims, 16 Drawing Sheets

Related U.S. Application Data

(60) Provisional application No. 62/358,231, filed on Jul. 5, 2016, provisional application No. 62/425,560, filed on Nov. 22, 2016, provisional application No. 62/456,217, filed on Feb. 8, 2017, provisional application No. 62/458,975, filed on Feb. 14, 2017.

(51) Int. Cl.

| | | |
|---|---|---|
| *A61F 2/00* | (2006.01) | |
| *A61B 17/04* | (2006.01) | |
| *A61B 17/06* | (2006.01) | |
| *A61B 17/16* | (2006.01) | |
| *A61B 90/00* | (2016.01) | |
| *A61B 17/88* | (2006.01) | |
| *A61B 17/80* | (2006.01) | |
| *A61B 17/00* | (2006.01) | |
| *A61B 17/84* | (2006.01) | |

(52) U.S. Cl.
CPC ........ *A61B 17/1604* (2013.01); *A61B 17/885* (2013.01); *A61B 17/8869* (2013.01); *A61B 90/06* (2016.02); *A61B 17/80* (2013.01); *A61B 17/848* (2013.01); *A61B 2017/00526* (2013.01); *A61B 2017/00867* (2013.01); *A61B 2017/0403* (2013.01); *A61B 2017/0404* (2013.01); *A61B 2017/044* (2013.01); *A61B 2017/045* (2013.01); *A61B 2017/0409* (2013.01); *A61B 2017/0414* (2013.01); *A61B 2017/0441* (2013.01); *A61B 2017/0445* (2013.01); *A61B 2017/0453* (2013.01); *A61B 2017/0464* (2013.01); *A61B 2090/061* (2016.02)

(56) References Cited

U.S. PATENT DOCUMENTS

| | | |
|---|---|---|
| 2,362,957 A | 11/1944 | Hackett |
| 2,427,128 A | 9/1947 | Ettinger |
| 2,485,531 A | 10/1949 | William |
| 2,489,870 A | 11/1949 | William |
| 2,511,051 A | 6/1950 | William |
| 2,706,475 A | 4/1955 | Reynolds |
| 2,715,403 A | 8/1955 | Jordan |
| 3,114,367 A | 12/1963 | Carpenter |
| 3,664,022 A | 5/1972 | Small |
| 3,727,611 A | 4/1973 | Schultz |
| 3,867,932 A | 2/1975 | Huene |
| 3,959,960 A | 6/1976 | Santos |
| 4,050,464 A | 9/1977 | Hall |
| 4,159,716 A | 7/1979 | Borchers |
| 4,364,381 A | 12/1982 | Sher |
| D273,326 S | 4/1984 | Peterson |
| 4,586,497 A | 5/1986 | Dapra |
| 4,587,963 A | 5/1986 | Leibinger |
| 4,712,542 A | 12/1987 | Daniel |
| 4,787,377 A | 11/1988 | Laboureau |
| 4,945,904 A | 8/1990 | Bolton |
| 4,964,862 A | 10/1990 | Arms |
| 4,969,471 A | 11/1990 | Daniel |
| 4,969,895 A | 11/1990 | McLeod |
| 5,035,701 A | 7/1991 | Kabbara |
| 5,116,340 A | 5/1992 | Songer |
| 5,300,077 A | 4/1994 | Howell |
| 5,306,290 A | 4/1994 | Martins |
| 5,312,410 A | 5/1994 | Miller |
| 5,312,412 A | 5/1994 | Whipple |
| 5,409,490 A | 4/1995 | Ethridge |
| 5,431,659 A | 7/1995 | Ross, Jr. |
| 5,449,361 A | 9/1995 | Preissman |
| 5,476,465 A | 12/1995 | Preissman |
| 5,540,698 A | 7/1996 | Preissman |
| 5,545,168 A | 8/1996 | Burke |
| 5,570,706 A | 11/1996 | Howell |
| 5,578,057 A | 11/1996 | Wenstrom, Jr. |
| 5,584,839 A | 12/1996 | Gieringer |
| 5,643,321 A | 1/1997 | McDevitt |
| 5,702,397 A | 12/1997 | Goble et al. |
| 5,713,897 A | 2/1998 | Goble |
| 5,725,532 A | 3/1998 | Shoemaker |
| 5,741,281 A | 4/1998 | Martin |
| 5,868,748 A | 2/1999 | Burke |
| 5,895,389 A | 4/1999 | Schenk |
| 6,001,106 A | 12/1999 | Ryan |
| 6,027,523 A | 2/2000 | Schmieding |
| 6,045,573 A | 4/2000 | Wenstrom |
| 6,254,604 B1 | 7/2001 | Howell |
| 6,254,605 B1 | 7/2001 | Howell |
| 6,368,326 B1 | 4/2002 | Dakin |
| 6,443,955 B1 | 9/2002 | Ahrend |
| 6,478,753 B2 | 11/2002 | Reay |
| 6,482,208 B1 | 11/2002 | Ahrend |
| 6,517,564 B1 | 2/2003 | Grafton |
| 6,527,794 B1 | 3/2003 | McDevitt |
| 6,547,778 B1 | 4/2003 | Sklar |
| 6,554,852 B1 | 4/2003 | Oberlander |
| 6,557,426 B2 | 5/2003 | Reinemann, Jr. |
| 6,616,667 B1 | 9/2003 | Steiger |
| 6,660,023 B2 | 12/2003 | McDevitt |
| 6,669,698 B1 | 12/2003 | Tromanhauser |
| 6,739,068 B1 | 5/2004 | Rinner |
| 6,761,722 B2 | 7/2004 | Cole |
| 6,780,198 B1 | 8/2004 | Gregoire |
| 6,866,673 B2 | 3/2005 | Oren |
| 7,060,068 B2 | 6/2006 | Tromanhauser |
| 7,081,126 B2 | 7/2006 | McDevitt |
| 7,083,638 B2 | 8/2006 | Foerster |
| 7,090,690 B2 | 8/2006 | Foerster |
| 7,160,285 B2 | 1/2007 | Sklar |
| 7,172,626 B1 | 2/2007 | Andrews |
| 7,211,088 B2 | 5/2007 | Grafton |
| 7,226,469 B2 | 6/2007 | Benavitz |
| 7,235,091 B2 | 6/2007 | Thornes |
| 7,326,222 B2 | 2/2008 | Dreyfuss |
| 7,431,692 B2 | 10/2008 | Zollinger |
| 7,442,202 B2 | 10/2008 | Dreyfuss |
| 7,455,683 B2 | 11/2008 | Geissler |
| 7,537,596 B2 | 5/2009 | Jensen |
| 7,556,630 B2 | 7/2009 | Molz |
| 7,572,275 B2 | 8/2009 | Fallin |
| 7,578,824 B2 | 8/2009 | Justin |
| 7,637,926 B2 | 12/2009 | Foerster |
| 7,871,368 B2 | 1/2011 | Zollinger |
| 7,875,058 B2 | 1/2011 | Holmes, Jr. |
| 7,887,551 B2 | 2/2011 | Bojarski |
| 7,901,431 B2 | 3/2011 | Shumas |
| 7,963,966 B2 | 6/2011 | Cole |
| 7,998,149 B2 | 8/2011 | Hamilton |
| 8,083,769 B2 | 12/2011 | Cauldwell |
| 8,109,936 B2 | 2/2012 | Tipirneni |
| 8,114,127 B2 | 2/2012 | West |
| 8,114,128 B2 | 2/2012 | Cauldwell |
| 8,162,997 B2 | 4/2012 | Struhl |
| 8,167,906 B2 | 5/2012 | Cauldwell |
| 8,182,495 B2 | 5/2012 | DiStefano |
| 8,221,455 B2 | 7/2012 | Shurnas |
| 8,277,459 B2 | 10/2012 | Sand |
| 8,277,484 B2 | 10/2012 | Barbieri |
| 8,298,247 B2 | 10/2012 | Sterrett |
| 8,303,591 B1 | 11/2012 | Foerster |
| 8,317,828 B2 | 11/2012 | Martinek |
| 8,343,186 B2 | 1/2013 | Dreyfuss |
| 8,394,123 B2 | 3/2013 | Cauldwell |
| 8,414,599 B1 | 4/2013 | Foerster |
| 8,460,379 B2 | 6/2013 | Albertorio |
| 8,500,745 B2 | 8/2013 | Kuenzi |
| 8,506,597 B2 | 8/2013 | Kaiser |
| 8,579,901 B1 | 11/2013 | Foerster |
| 8,597,328 B2 | 12/2013 | Cauldwell |
| 8,613,755 B1 | 12/2013 | Foerster |
| 8,617,185 B2 | 12/2013 | Bonutti |
| 8,623,049 B2 | 1/2014 | Ward |

(56) References Cited

U.S. PATENT DOCUMENTS

| | | |
|---|---|---|
| 8,623,051 B2 | 1/2014 | Bojarski |
| 8,623,052 B2 | 1/2014 | Dreyfuss |
| 8,679,122 B2 | 3/2014 | Bernstein |
| 8,696,719 B2 | 4/2014 | Lofthouse |
| 8,715,297 B1 | 5/2014 | Foerster |
| 8,764,763 B2 | 7/2014 | Foerster |
| 8,764,797 B2 | 7/2014 | Dreyfuss |
| 8,790,344 B1 | 7/2014 | Foerster |
| 8,795,286 B2 | 8/2014 | Sand |
| 8,801,755 B2 | 8/2014 | Dreyfuss |
| 8,814,902 B2 | 8/2014 | Bonutti |
| 8,821,541 B2 | 9/2014 | Dreyfuss |
| 8,870,876 B2 | 10/2014 | Lettmann |
| 8,876,900 B2 | 11/2014 | Guederian |
| 8,882,833 B2 | 11/2014 | Saylor |
| 8,888,815 B2 | 11/2014 | Holmes, Jr. |
| 8,926,626 B2 | 1/2015 | Mannava |
| 8,939,999 B2 | 1/2015 | Sterrett |
| 8,945,026 B2 | 2/2015 | Moser |
| 8,961,575 B2 | 2/2015 | Choinski |
| 8,979,850 B2 | 3/2015 | Johnstone |
| 8,984,720 B2 | 3/2015 | Gephart |
| 9,017,330 B2 | 4/2015 | Foerster |
| 9,039,682 B2 | 5/2015 | Lampropoulos et al. |
| 9,072,509 B2 | 7/2015 | Stoll, Jr. |
| 9,107,701 B2 | 8/2015 | Cole |
| 9,131,937 B2 | 9/2015 | Chan |
| 9,138,219 B2 | 9/2015 | Horrell |
| 9,161,748 B2 | 10/2015 | West |
| 9,179,907 B2 | 11/2015 | ElAttrache |
| 9,179,950 B2 | 11/2015 | Zajac |
| 9,186,133 B2 | 11/2015 | Gregoire |
| 9,204,872 B2 | 12/2015 | Loepke |
| 9,259,217 B2 | 2/2016 | Fritzinger |
| 9,271,715 B2 | 3/2016 | Cauldwell |
| 9,277,912 B2 | 3/2016 | Donate |
| 9,521,999 B2 | 12/2016 | Dreyfuss |
| 9,526,493 B2 | 12/2016 | Dreyfuss |
| 9,532,776 B2 | 1/2017 | Lo |
| 9,549,726 B2 | 1/2017 | Dreyfuss |
| 9,622,739 B2 | 4/2017 | Dreyfuss |
| 2001/0049483 A1 | 12/2001 | Reay |
| 2002/0087190 A1 | 7/2002 | Benavitz |
| 2002/0188297 A1 | 12/2002 | Dakin |
| 2003/0009171 A1 | 1/2003 | Tornier |
| 2003/0176920 A1 | 9/2003 | Sklar |
| 2004/0098045 A1 | 5/2004 | Grafton |
| 2004/0102788 A1 | 5/2004 | Huebner |
| 2004/0153153 A1 | 8/2004 | Elson |
| 2005/0065533 A1 | 3/2005 | Magen |
| 2005/0070906 A1 | 3/2005 | Clark |
| 2005/0222618 A1 | 10/2005 | Dreyfuss |
| 2005/0240226 A1 | 10/2005 | Foerster |
| 2006/0085006 A1 | 4/2006 | Ek |
| 2006/0161159 A1 | 7/2006 | Dreyfuss |
| 2006/0229623 A1* | 10/2006 | Bonutti .............. A61B 17/844 606/74 |
| 2006/0271060 A1 | 11/2006 | Gordon |
| 2006/0276804 A1 | 12/2006 | Molz |
| 2006/0293709 A1 | 12/2006 | Bojarski |
| 2007/0060922 A1 | 3/2007 | Dreyfuss |
| 2007/0060931 A1 | 3/2007 | Hamilton |
| 2007/0073299 A1 | 3/2007 | Dreyfuss |
| 2007/0083236 A1 | 4/2007 | Sikora |
| 2007/0088362 A1 | 4/2007 | Bonutti |
| 2007/0150003 A1 | 6/2007 | Dreyfuss |
| 2007/0198036 A1 | 8/2007 | Sklar |
| 2007/0225764 A1 | 9/2007 | Benavitz |
| 2007/0288027 A1 | 12/2007 | Grafton |
| 2008/0077182 A1 | 3/2008 | Geissler |
| 2008/0249567 A1 | 10/2008 | Kaplan |
| 2009/0043153 A1 | 2/2009 | Zollinger |
| 2009/0228049 A1 | 9/2009 | Park |
| 2009/0306711 A1 | 12/2009 | Stone et al. |
| 2010/0010496 A1 | 1/2010 | Isaza |
| 2010/0160963 A1 | 6/2010 | Fallin |
| 2010/0191284 A1 | 7/2010 | Dreyfuss |
| 2010/0262185 A1 | 10/2010 | Gelfand |
| 2011/0022054 A1 | 1/2011 | DiStefano |
| 2011/0112576 A1 | 5/2011 | Nguyen |
| 2011/0184426 A1 | 7/2011 | Garces Martin |
| 2011/0224727 A1 | 9/2011 | Housman |
| 2012/0053626 A1 | 3/2012 | Koepke |
| 2012/0060847 A1 | 3/2012 | Stratton |
| 2012/0065677 A1 | 3/2012 | West |
| 2012/0123417 A1 | 5/2012 | Smith |
| 2012/0123428 A1 | 5/2012 | Berberich |
| 2012/0165867 A1 | 6/2012 | Denham et al. |
| 2012/0172936 A1 | 7/2012 | Horrell |
| 2012/0253410 A1 | 10/2012 | Taylor |
| 2013/0023930 A1 | 1/2013 | Stone et al. |
| 2013/0138150 A1 | 5/2013 | Baker |
| 2013/0165972 A1 | 6/2013 | Sullivan |
| 2013/0184708 A1 | 7/2013 | Robinson |
| 2013/0296937 A1 | 11/2013 | Dreyfuss |
| 2013/0345750 A1 | 12/2013 | Sullivan |
| 2014/0018828 A1 | 1/2014 | Foerster |
| 2014/0031882 A1 | 1/2014 | Schmuck |
| 2014/0039551 A1 | 2/2014 | Donahue |
| 2014/0074163 A1 | 3/2014 | West |
| 2014/0081322 A1 | 3/2014 | Sengun |
| 2014/0081323 A1 | 3/2014 | Hawkins |
| 2014/0081324 A1 | 3/2014 | Sengun |
| 2014/0081325 A1 | 3/2014 | Sengun |
| 2014/0114353 A1 | 4/2014 | Bojarski |
| 2014/0121701 A1 | 5/2014 | Dreyfuss |
| 2014/0128915 A1 | 5/2014 | Dreyfuss |
| 2014/0194907 A1 | 7/2014 | Bonutti |
| 2014/0194927 A1 | 7/2014 | Kaiser |
| 2014/0277134 A1 | 9/2014 | ElAttrache |
| 2014/0364905 A1 | 12/2014 | Lunn |
| 2014/0364909 A1 | 12/2014 | Dreyfuss |
| 2014/0371749 A1 | 12/2014 | Foerster |
| 2014/0379028 A1 | 12/2014 | Lo |
| 2015/0005779 A1 | 1/2015 | Tepic |
| 2015/0005819 A1 | 1/2015 | Dreyfuss |
| 2015/0012015 A1 | 1/2015 | Berelsman |
| 2015/0039029 A1 | 2/2015 | Wade |
| 2015/0051601 A1 | 2/2015 | Larsen |
| 2015/0073475 A1 | 3/2015 | Schaller |
| 2015/0073477 A1 | 3/2015 | Holmes, Jr. |
| 2015/0173739 A1 | 6/2015 | Rodriguez et al. |
| 2015/0201923 A1 | 7/2015 | Fan |
| 2015/0216576 A1 | 8/2015 | Foerster |
| 2015/0272567 A1 | 10/2015 | Feezor |
| 2015/0289868 A1 | 10/2015 | Sauer |
| 2015/0305737 A1 | 10/2015 | Conley |
| 2015/0313640 A1 | 11/2015 | O'Daly |
| 2015/0342594 A1 | 12/2015 | Stone |
| 2015/0342596 A1 | 12/2015 | Dreyfuss |
| 2015/0342651 A1 | 12/2015 | Cole |
| 2015/0351741 A1 | 12/2015 | Hawkins |
| 2016/0008041 A1 | 1/2016 | Makhlouf |
| 2016/0038186 A1 | 2/2016 | Herzog et al. |
| 2016/0038201 A1 | 2/2016 | Cummings |
| 2016/0038267 A1 | 2/2016 | Allen |
| 2016/0051250 A1 | 2/2016 | Thornes |
| 2016/0051251 A1 | 2/2016 | Koepke |
| 2016/0066901 A1 | 3/2016 | Gregoire |
| 2016/0089131 A1 | 3/2016 | Wade |
| 2016/0192924 A1 | 7/2016 | Cauldwell |
| 2016/0235399 A1 | 8/2016 | Housman |
| 2016/0270902 A1 | 9/2016 | Snedeker et al. |
| 2016/0287302 A1 | 10/2016 | Horrell |
| 2016/0374661 A1 | 12/2016 | Housman et al. |
| 2017/0071592 A1 | 3/2017 | Feezor et al. |

FOREIGN PATENT DOCUMENTS

| | | |
|---|---|---|
| ES | 2226791 T3 | 4/2005 |
| JP | 2002102236 A | 4/2002 |
| WO | 2007102829 A1 | 9/2007 |

(56) References Cited

FOREIGN PATENT DOCUMENTS

| WO | 2011153417 A1 | 12/2011 |
| WO | 2012092027 A2 | 7/2012 |

OTHER PUBLICATIONS

Deltoid Ligament Reconstruction Tunnel Sites, Arthrex, Inc., www.arthrex.com, 2014, 2 pp.
InternalBrace—Ligament Augmentaion Repair—Deltoid Ligament, Arthex, Inc., www.arthrex.com, 2015, 2 pp.
InternalBrace—Advanced Treatment for Ligament & Tendon Repair, Arthrex, Inc., www.arthrex.com, 2 pp.
InternalBrace—Ligament Augmentation Repair, Arthrex, Inc., www.arthrex.com, 2015, 2 pp.
Modified Brostrom-Gould Technique for Lateral Ankle Ligament Reconstruction—Surgical Technique, Arthrex, Inc., www.arthrex.com, 2015, 6 pp.
Knotless TightRope Syndesmosis Fixation—Surgical Technique, Arthrex, Inc., www.arthrex.com, 2015, 5 pp.
Get your athlete back in the game!—Syndesmosis TightRope, Arthrex, Inc., http://cptr.it/TRHAS, 2015, 1 pp.
ZipTight Fixation System, BioMet Sports Medicine, www.biometsportsmedicine.com, 2009, 8 pp.
Nelson, Owen A., "Examination and Repair of the AITFL in Transmalleolar Fractures", J. Orthop Trauma, vol. 20, No. 9, Oct. 2006, p. 637-643.
Invisiknot—Foot and Ankle Technique Guide—Ankle Syndesmosis Repair, Operative Technique, Smith & Nephew, Inc., www.smith-nephew.com, Jun. 2017, 8 pp.
Invisiknot—Ankle Syndesmosis Repair Kit, Smith & Nephew, Inc., www.smith-nephew.com, 1 pp.
Van Heest, Tyler J., et al., "Injuries to the Ankle Syndesmosis", J. Bone Joint Surg. Am. 2014;96:603-13, http://dx.dor.org/10.2106/JBJS.M.00094, 11 pp.
International Search Report and Written Opinion for Int. Appl. No. PCT/US2017/064173 dated Feb. 14, 2018, 8 pp.
International Search Report and Written Opinion for Int. Appl. No. PCT/US2017/064178 date Mar. 9, 2018, 9 pp.

* cited by examiner

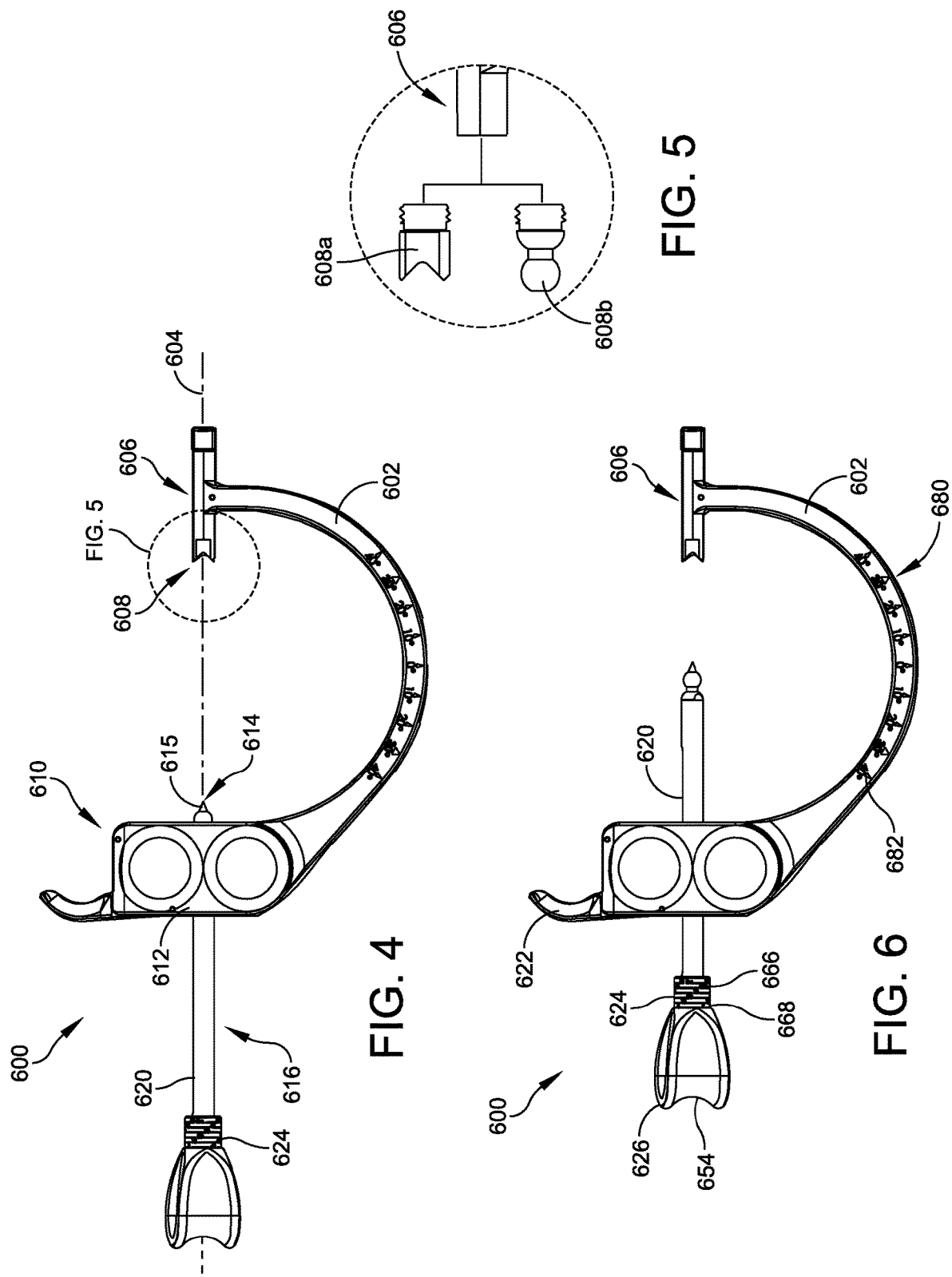

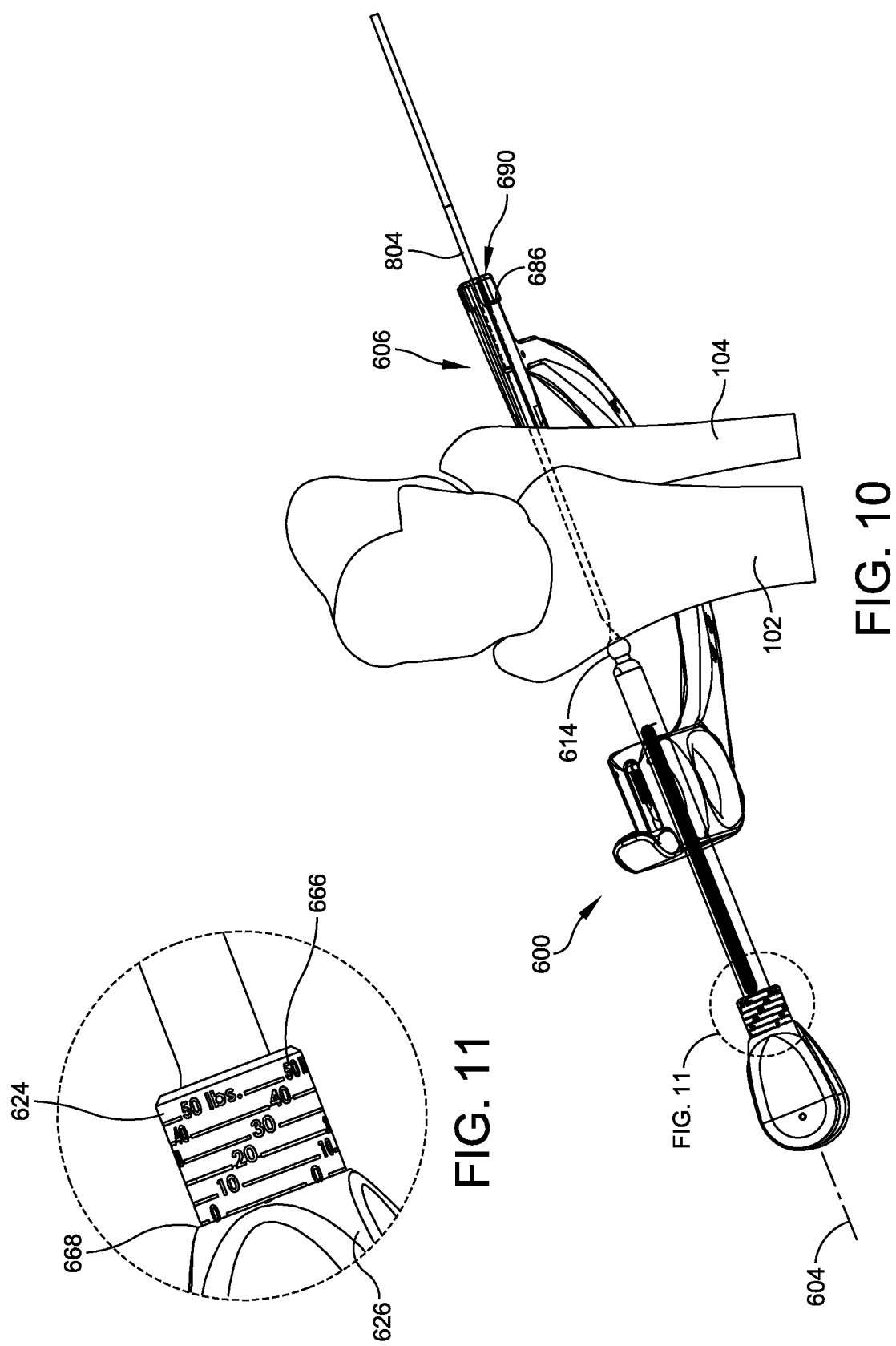

COMPRESSION AND TENSION INSTRUMENTS AND METHODS OF USE TO REINFORCE LIGAMENTS

REFERENCE TO PENDING PRIOR PATENT APPLICATIONS

This application claims the benefit under 35 U.S.C. 119(e) of U.S. Provisional Patent Application Nos. 62/358,231, filed Jul. 5, 2016 by Justin Taber and T. Wade Fallin for "LIGAMENT REINFORCEMENT DEVICES AND METHODS," 62/425,560 filed Nov. 22, 2016 by Justin Tabor, Phinit Phisitkul, and T. Wade Fallin for "LIGAMENT REINFORCEMENT DEVICES AND METHODS," 62/456,217, filed Feb. 8, 2017 by Justin Taber and T. Wade Fallin for "PLATE AND LOOP CONSTRUCT," and 62/458,975, filed Feb. 14, 2017 by Matthew Karam, Phinit Phisitkul, Justin Taber, and T. Wade Fallin for "PELVIC FRACTURE REPAIR," all of which patent applications are hereby incorporated herein by reference.

REFERENCE TO CO-FILED APPLICATIONS

This application was co-filed with the following U.S. patent application Numbers on Jul. 5, 2017: Ser. No. 15/641,573, by T. Wade Fallin, Justin Taber, Matthew Karam, and Phinit Phisitkul for "INTRA JOINT STABILIZATION CONSTRUCT," Ser. No. 15/641,592 by T. Wade Fallin, Justin Taber, Matthew Karam, and Phinit Phisitkul for "EXTRA JOINT STABILIZATION CONSTRUCT," Ser. No. 15/641,600 by Justin Taber and T. Wade Fallin for "NONCIRCULAR BROACH AND METHODS OF USE," and Ser. No. 15/641,618 by Phinit Phisitkul, Justin Taber, and T. Wade Fallin for "MULTIPLE SUTURE THREADER AND METHODS OF USE," all of which patent applications are incorporated herein by reference.

BACKGROUND

Ligaments interconnect bones of the skeletal system and are involved with the stabilization and kinematics of skeletal joints. Various injuries may occur that result in compromised ligament function. Such injuries include, for example, partial and complete tears and avulsion of the bone where a ligament attaches to a bone. Ligament injuries occur throughout the skeletal system.

By way of example, the human ankle 100 is a complex junction of multiple bones and soft tissues, as shown in FIGS. 1-3. The ankle 100 includes joints between the tibia 102, fibula 104, and talus 106. The joint between the tibia 102 and fibula 104 is a syndesmosis or slightly movable joint in which the bones are joined together by connective tissue. The syndesmosis between the tibia 102 and fibula 104 includes the anterior inferior tibiofibular ligament (AITFL) 110, the posterior inferior tibiofibular ligament (PITFL) 112, and the interosseous ligament (IOL) 114. The syndesmosis ligaments are often injured in high ankle sprains. Other injury prone ligaments of the ankle joint include, among others, the anterior talofibular ligament (ATFL) 120, the posterior talofibular ligament (PTFL) 122 and the deltoid ligament complex 124 including superficial and deep deltoid ligaments. Current implants, instruments, and methods used to reinforce ligaments to promote healing and normal joint function present a number of challenges, and improvements are needed.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

One embodiment provides a clamp for compressing first and second bone portions together to reduce a space therebetween. The clamp includes a body comprising opposing first and second ends, the first and second ends comprising respective first and second jaws that define a longitudinal clamp axis, the first jaw engageable with the first bone portion and the second jaw engageable with the second bone portion to define a directional force vector between the first and the second bone portions that is coaxial with the longitudinal clamp axis. The clamp also includes an adjustment mechanism coupled with the second jaw and configured to translate the second jaw distally toward the first jaw along the longitudinal axis to compress the first and the second bone portions between the first and the second jaws. The adjustment mechanism includes a force gauge configured to indicate a compression force placed upon the first and the second bone portions by the first and the second jaws along the directional force vector.

Another embodiment provides a tension instrument for tensioning and knotlessly locking a flexible strand having first and second opposing flexible strand ends, where the first flexible strand end is fixed adjacent to a first member, and the second flexible strand end is free proximal to the first member and adjacent to a second member. The tension instrument comprises a member engagement feature configured to engage with the second member through which the second flexible strand end passes and an adjustment mechanism operably coupled to a proximal end of the member engagement feature. The adjustment mechanism includes (a) a selectively adjustable flexible strand clamp configured to capture the second flexible strand end and translate the second flexible strand end proximally relative to the member engagement feature to place a tensile force on the flexible strand between the first and the second members; (b) a force gauge operably coupled with the selectively adjustable flexible strand clamp, the force gauge including force indicia to provide an indication of the tensile force placed on the flexible strand; and (c) a pathway extending through the adjustment mechanism from a proximal end to a distal end adjacent the member engagement feature to provide clearance for fixation hardware that knotlessly locks the second flexible strand end relative to the second member to maintain the tensile force between the first and the second flexible strand ends.

Yet another embodiment provides a method of reinforcing a syndesmosis joint of a patient using: (a) a clamp having first and second opposing jaws that define a longitudinal clamp axis, an angle gauge configured to set an angle of the longitudinal clamp axis relative to a reference line of a patient's anatomy, and an adjustment mechanism configured to apply a measurable compression force along a directional force vector between the first and the second clamp jaws that is coaxial with the longitudinal clamp axis; and (b) a tension instrument having an anchor engagement feature coupled with an adjustment mechanism configured place a measurable tensile force on a flexible strand extending between a first anchor in a first bone portion and a second anchor in a second bone portion. The method includes the steps of (i) using the angle gauge, positioning the clamp such that the first jaw is engaged with the first bone portion and the second jaw is engaged with the second bone portion at a desired angle of the directional force vector relative to the reference line of the patient's anatomy; (ii) actuating the adjustment mechanism of the clamp to translate the second jaw of the clamp distally to achieve a desired compression force between the first and the second bone portions along the directional force vector; (iii) noting the desired compression force reflected upon a force gauge of the adjustment mechanism of the clamp; (iv) inserting a guide along the longitudinal clamp axis through the first jaw and into the first and the second bone portions to form a bone tunnel extending between the first and the second bone portions; (v) removing the clamp, leaving the guide in position; (vi) affixing a first end of a flexible strand to a first fixation anchor; (vii) using the guide, pulling a second end of the flexible strand through the bone tunnel to insert the first fixation anchor into the bone tunnel at the second bone portion; (viii) threading the second end of the flexible strand flexible strand through a second fixation anchor; (ix) inserting the second fixation anchor into the bone tunnel at the first bone portion; (x) engaging the anchor engagement feature of the tension instrument with the second fixation anchor; (xi) using the adjustment mechanism of the tension instrument, pulling the second end of the flexible strand until a desired tensile force is placed on the flexible strand between the first and the second bone portions, as reflected upon a force gauge of the adjustment mechanism of the tension instrument, wherein the desired tensile force equals the desired compression force applied through the clamp; and (xii) accessing the second fixation anchor through a pathway through the tension instrument, knotlessly locking the second end of the flexible strand in relation to the second fixation anchor.

Additional objects, advantages and novel features of the technology will be set forth in part in the description which follows, and in part will become more apparent to those skilled in the art upon examination of the following, or may be learned from practice of the technology.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified. Illustrative embodiments of the invention are illustrated in the drawings, in which:

FIG. 4 illustrates a front view of one embodiment of a clamp instrument for compressing two bone portions together;

FIG. 5 illustrates two alternative embodiments of a first jaw of the clamp instrument of FIG. 4;

FIG. 6 illustrates another front view of the clamp instrument of FIG. 4;

FIG. 10 illustrates the clamp instrument of FIG. 4 with a patient's tibia and fibula compressed therebetween;

FIG. 11 illustrates a perspective view of a force gauge of the clamp instrument of FIG. 4;

DETAILED DESCRIPTION

Figure 1:
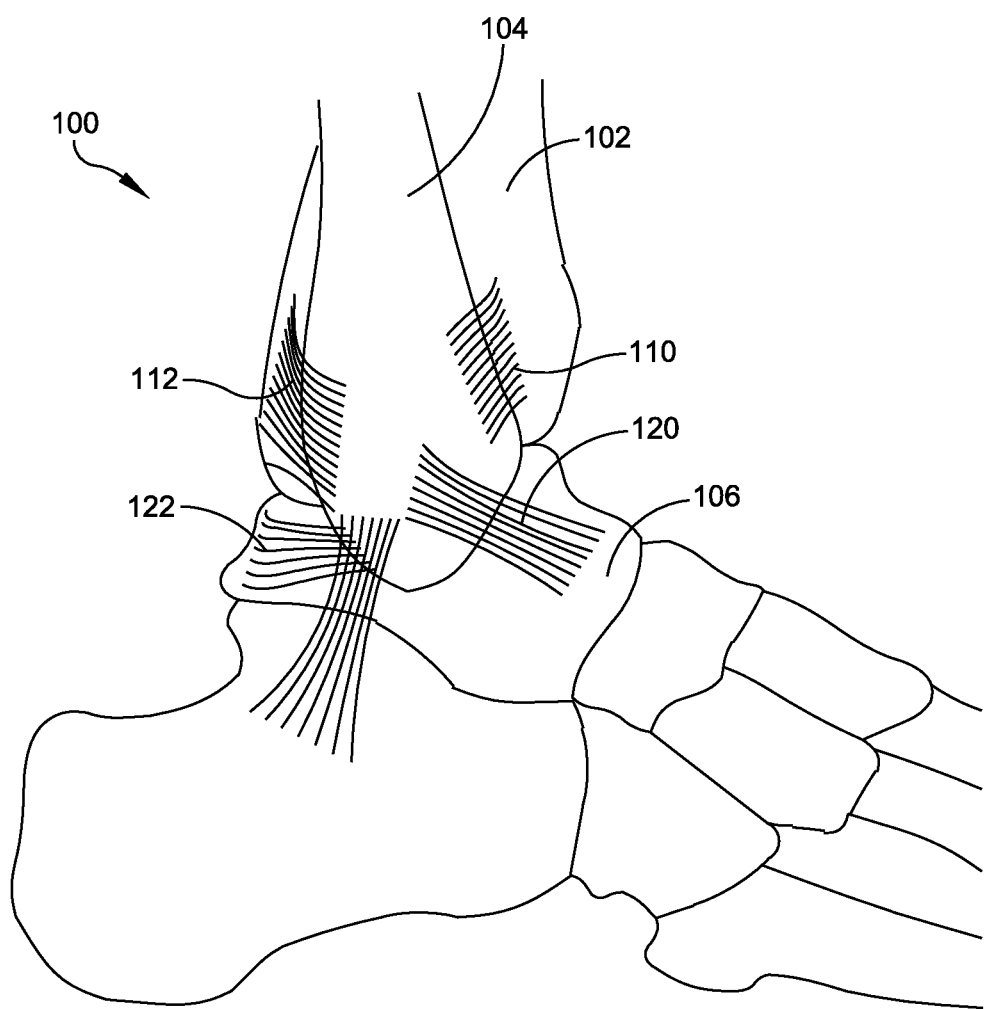
FIG. 1 illustrates a right view of a human ankle joint.
Figure 2:
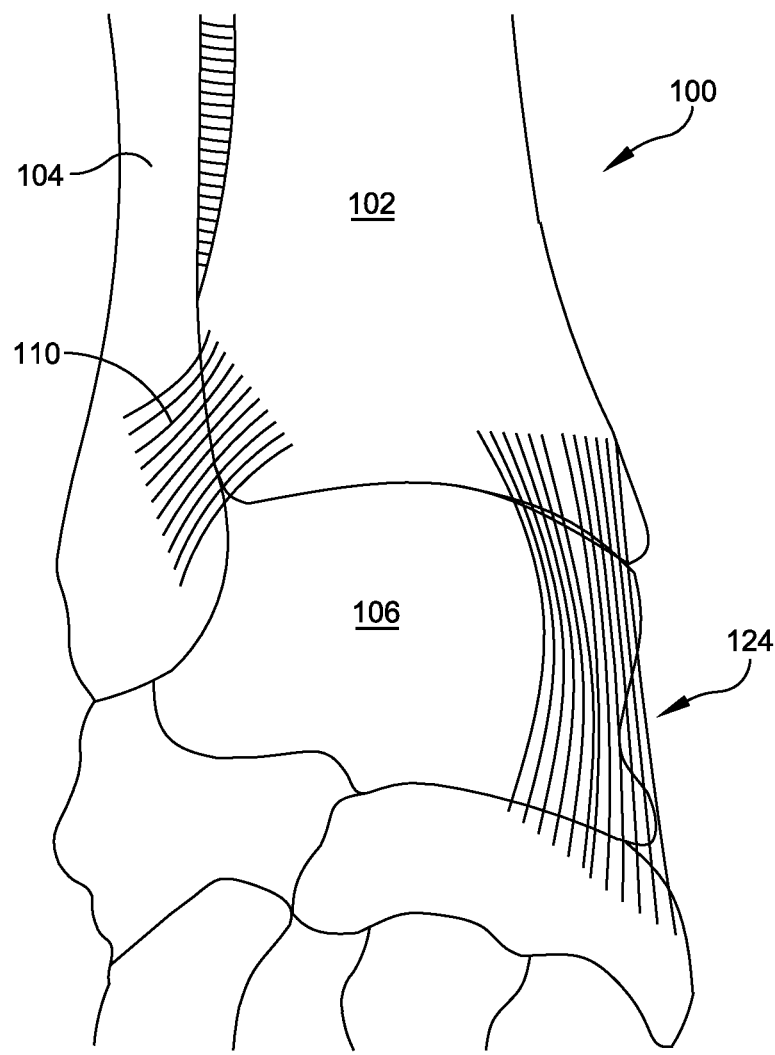
FIG. 2 illustrates a front view of a human ankle joint.

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

The technology discussed herein relates to apparatus and corresponding methods of use for preparing ligament reinforcement constructs. In one embodiment, a compression instrument, or clamp, provides a mechanism for clamping bone portions together to reduce the space therebetween with a force vector having both a known direction and a known magnitude. Embodiments of the clamp may provide a pin guide for inserting a pin coaxial with the force vector and may include features to facilitate rapid application of clamping pressure as well as fine tuning of the clamping pressure. Embodiments of the clamp may provide multiple modes of operation, including one-way incremental clamping and dynamic, continuously adjustable clamping. In other embodiments, the clamp may include a quick release mechanism to release clamping pressure. The clamp may also include a depth gauge for indicating the length of a path through a bone coaxial with the force vector.

FIGS. 4-11 illustrate one exemplary embodiment of a compression instrument or clamp 600 having a bow-shaped body 602 defining a longitudinal clamp axis 604. A first end 606 of the body 602 includes a first jaw 608 that extends proximally toward a second end 610 of the body 602. As shown in FIG. 5, one embodiment of the first jaw 608 located at the first end 606 may feature a v-notch 608*a* that registers on and is engageable with a bone portion. In this embodiment, the first jaw 608 may be rigidly attached to the first end 606 and include the v-notch 608*a* formed by an angled opening directly engageable with a curved bone surface. The angled opening may be shaped to engage the shaft of a fibula, a malleolus, or any other desired bone location. For example, the first jaw 608 may be formed by making an angled cut through a tubular body to create the v-notched jaw 608*a* having opposed angled edges diverging toward the second end 610 of the body 602, as shown. In another embodiment, the first jaw 608 may feature a spherical end 608*b* configured to register on a bone plate. In both end embodiments 608*a-b*, the first jaw 608 is intersected by the clamp axis 604.

The second end 610 of the body 602 defines a receiver 612 able to mount a second jaw 614 for movement relative to the first jaw 608 along the clamp axis 604. In the example of FIGS. 4-11, the second jaw 614 includes a point contact element 615 engageable with a bone portion to define a directional vector between the first and the second jaws 608, 614, and thus the two bone portions, that is parallel or, as may be more specifically, coaxial with the clamp axis 604. The orientation is referred to hereinafter as "coaxial" but may be parallel as well. In the example of FIGS. 4-11, the point contact element 615 may form a sharpened spike able to engage with a bone surface.

Figure 7:
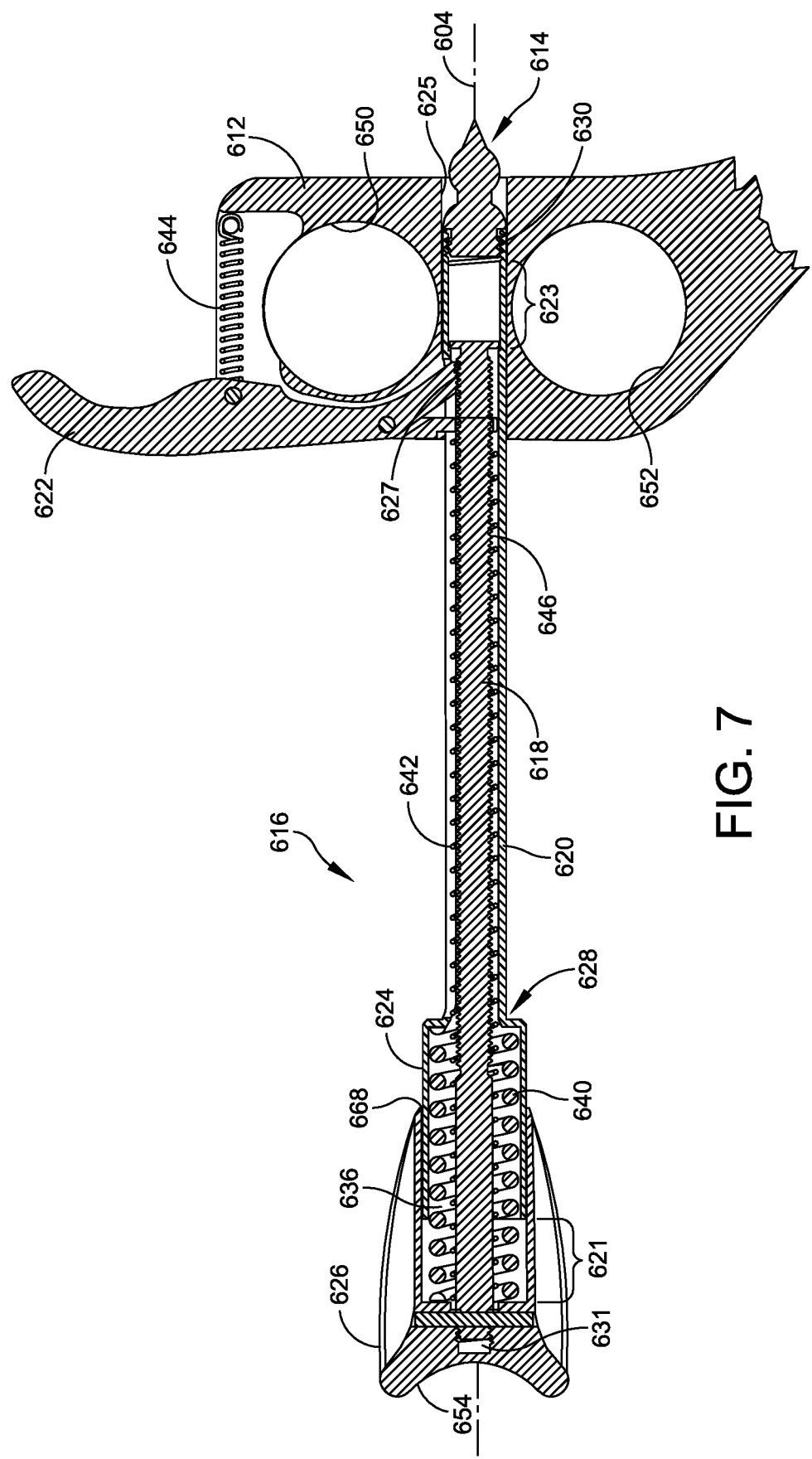
FIG. 7 illustrates a longitudinal cross-sectional view of an adjustment mechanism of the clamp instrument of FIG. 4.

In this embodiment, the second jaw 614 is mounted to an adjustment mechanism 616, detailed in the cross-sectional view of FIG. 7. The adjustment mechanism 616 includes an inner shaft 618, a hollow outer shaft 620 (i.e., sleeve), a release trigger 622, a force gauge 624, and a handle 626. The release trigger 622 is mounted in a translating relationship transverse to the clamp axis 604 and includes a screw thread 627 along its lower edge. The outer shaft 620 extends through a through hole 625 in the receiver 612 from a proximal end 628 to a distal end 630 coaxial with the clamp axis 604. The proximal end 628 of the outer shaft 620 is fixed to the force gauge 624. The inner shaft 618 is coaxially received within the outer shaft 620 and the force gauge 624 and is affixed to the handle 626 at its proximal end in an axial force and torque transmitting relationship via a pin 631. The second jaw 614 is mounted to the distal end 630 of the outer shaft 620. A first offset 621 separates the proximal end of the force gauge 624 and the proximal end of the inner shaft 618, and a second offset 623 separates the second jaw 614 from the distal end of the inner shaft 618.

The force gauge 624 is a hollow cylinder received within a gap 636 between the handle 626 and the inner shaft 618. A force spring 640 biases the force gauge 624 distally away from the handle 626; a return spring 642 biases the distal end of the inner shaft 618 proximally away from the receiver 612; and a trigger spring 644 biases the trigger partial threads 627 into engagement with external threads 646 formed on the inner shaft 618.

The receiver includes loops 650, 652 forming finger grips, and the handle 626 includes a groove 654 forming a thumb grip. In use, a user may place one or more fingers in the finger loops 650, 652 and apply pressure to the handle 626 with a thumb engaged in the thumb groove 654. This provides a syringe-like grip such that the handle 626 may be pressed distally. The threads 646 on the inner shaft 618 and the threads 627 on the lower portion of the trigger 622 are formed such that distal motion of the inner shaft 618 wedges or arcs the upper portion of the trigger 622 proximally, against the biasing of trigger spring 644, and allows the inner shaft 618 to ratchet forward (along with the outer shaft 620) upon the advancement of the handle 626 for gross adjustment control of the clamp 600.

To provide fine adjustment control of the clamp 600, the handle 626 may be rotated to minimally advance the inner and outer shafts 618, 620 by advancing the inner shaft threads 646 relative to the trigger threads 627. The threads 646 of the inner shaft 618 and the threads 627 of the lower portion of the trigger 622 engage to prevent proximal motion of the inner shaft 618 relative to the release trigger 622. A user may pull the release trigger 622 proximally to move or arc the trigger threads 627 upwardly and release the inner shaft 618 so that the inner shaft 618 and the outer shaft 620 may automatically be biased proximally by the return spring 642.

When the second jaw 614 engages another object (e.g., bone) that resists its distal motion relative to the first jaw 608, and the inner shaft 618 is advanced further, the handle 626 will advance over the casing of the force gauge 624 through the offset 621, thereby compressing the force spring 640 as the handle 626 moves over the force gauge 624. The amount of force required to advance the inner shaft 618, and thus the handle 626, distally is proportional to the distance the force spring is compressed from its resting position. Thus, the compression or joint reduction force placed upon the bone portions positioned between the first jaw 608 and the second jaw 614 is indicated by reading the force indicia 666 (e.g., 10 lbs., 20 lbs., 30 lbs.) on the force gauge 624 relative to an edge 668 of the handle, as detailed in FIGS. 10-11.

Figure 17:
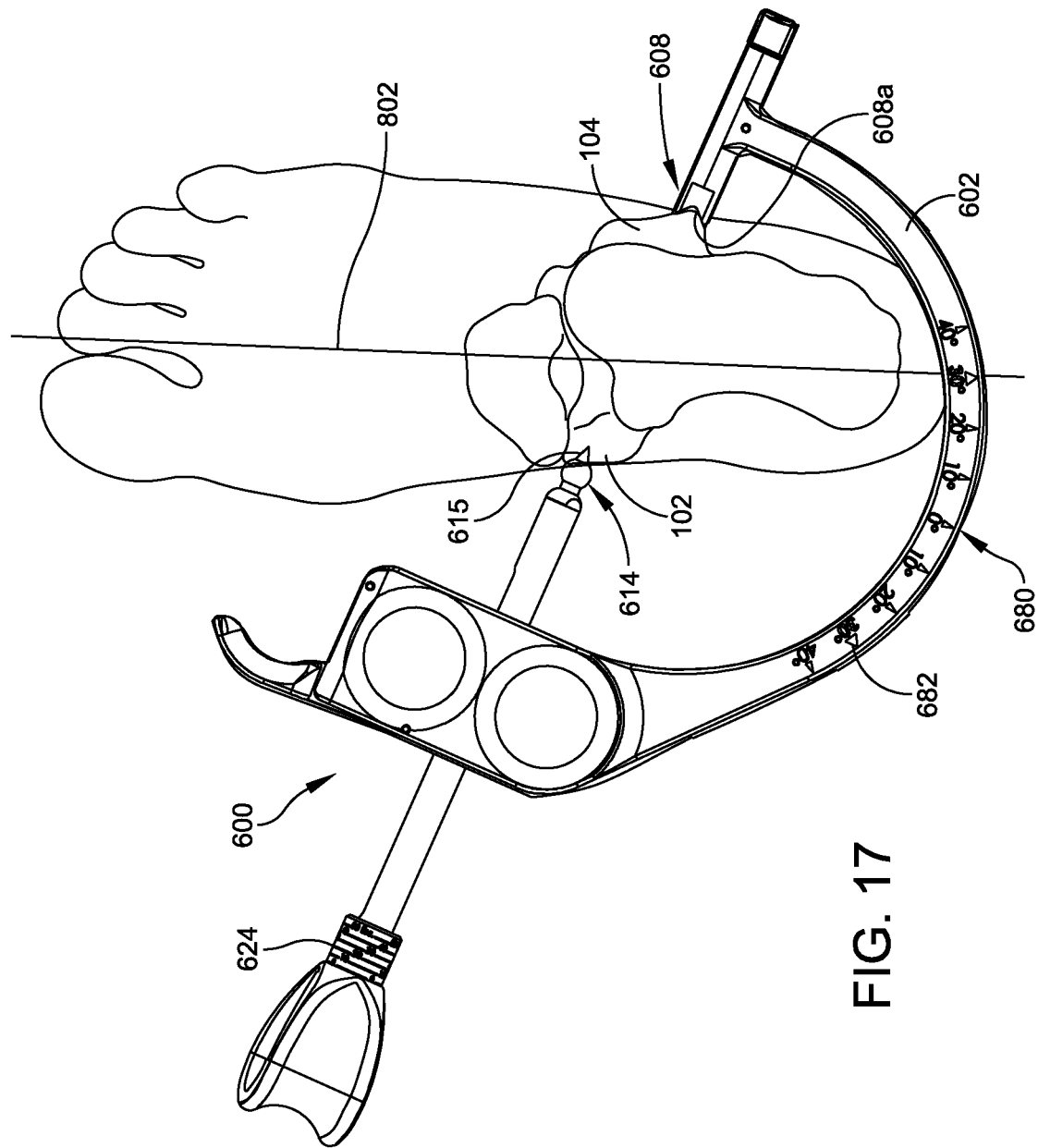
FIGS. 17-21 illustrate the operative steps described in the flowchart of FIG. 16.

In this embodiment, the body 602 of the clamp 600 includes an angle gauge 680 in the form of angle indicia 682 on a portion of the bow shaped body 602 between the first and second ends 606, 610. The indicia 682 are graduated so that a reference feature such as, for example, a reference line defined by portions of a patient's body, will align with the zero-degree mark when the reference line is perpendicular to the clamp axis 604. Angular marks on either side of the zero-degree mark indicate the amount of angular deviation of the reference line from the perpendicular, as shown in FIG. 17.

Using the angle gauge 680 in combination with the gauged clamping mechanism provided by the first and second jaws 608, 614, described above, the clamp 600 provides an optimal functional outcome that combines the compression or clamping of two bone portions together in the correct direction along an axis of the native ligament with an integrated force measurement that ensures the application of the correct clamping force needed to provide the requisite compression (e.g., oftentimes approximately 25-30 lbs. or, as commonly known in the industry, the approximate amount of force needed to crush an aluminum can).

Figure 9:
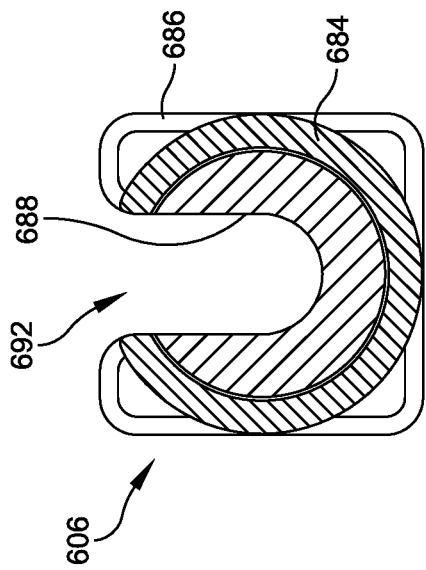
FIGS. 8-9 illustrate transverse cross-sectional views of a first end of the clamp instrument of FIG. 4 in respective closed and open configurations.
Figure 8:
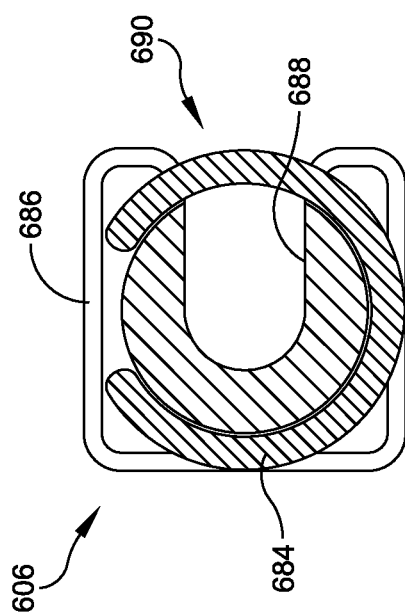

In the embodiment of FIGS. 4-11, the first end 606 of the body 602 includes a C-shaped arm 684, as shown in the lateral cross-sectional views of the first end 606 of FIGS. 8-9. A sheath 686 forming a U-shaped groove 688 is rotatively coupled about the C-shaped arm 684. When the sheath 686 is manually rotated into a closed configuration 690, shown in FIG. 8, the U-shaped groove 688 is blocked by the wall of the C-shaped arm 684, such that a user may use the blocked U-shaped groove 688 as a guide for the insertion of a drill, a length of k-wire, and/or a pin 804 into the bone portions compressed between the first and second jaws 608, 614 of the clamp 600, as shown in FIG. 10. Conversely, when the sheath 686 is manually rotated into an open configuration 692, shown in FIG. 9, the first end 606 of the clamp 600 essentially contains an open slot that allows the drill, length of k-wire, or pin 804 to pass unimpeded from the open U-shaped groove 688 in a direction transverse to the longitudinal clamp axis 604. As a result, the entire clamp 600 may disengaged from the bone portions clamped therein and transversely lifted away from the clamping site, leaving only the drill, k-wire, or pin 804 in place. In further detail and as shown in FIG. 10, when the sheath 686 is rotated into the closed configuration 690, the user may drill from a distal end of the first end 606 of the body 602 toward the bone portions clamped between the first and second jaws 608, 614. When the sheath 686 is rotated into the open configuration 692, the user may slip the drill or other hardware in a direction transverse to the axis 604 from the first end 606 of the clamp 600 through the open U-shaped groove 688 before disengaging the entire clamp 600 from the compressed bone portions and removing it from the clamp site. Using the closed and open configurations 690, 692 of the U-shaped groove 688, the clamp 600 may be employed in a variety of functional capacities, including the initial drilling of a bone tunnel, fixation of hardware, or as a stabilization device applied to realign bone tunnels after they have been drilled and have deviated from alignment.

Figure 12:
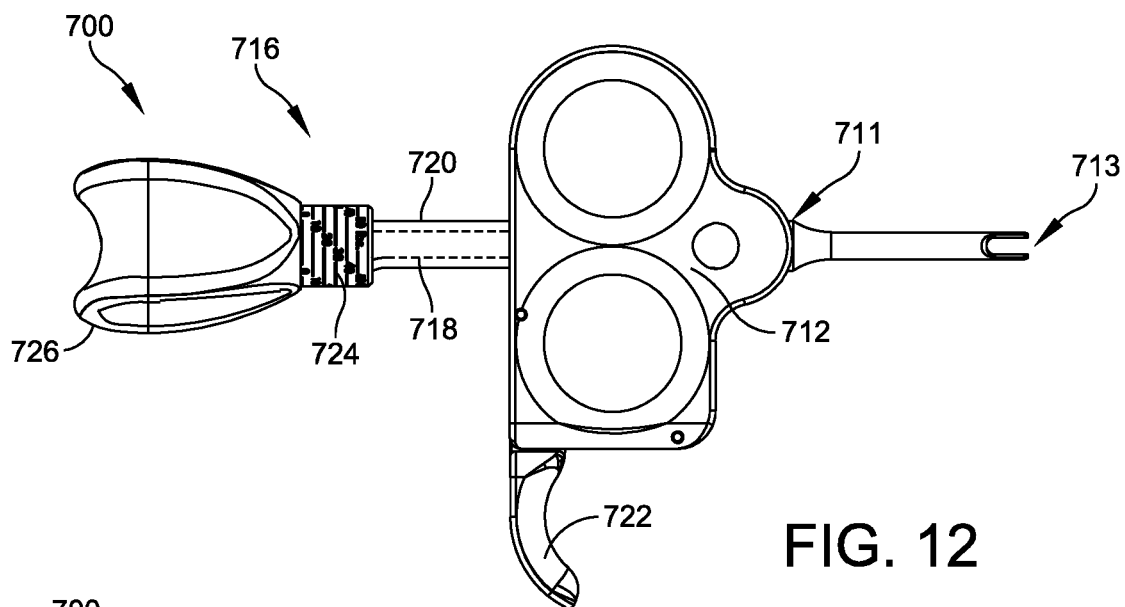
FIG. 12 illustrates a top view of a tension instrument for tensioning a flexible strand to a known amount of tension force.
Figure 13:
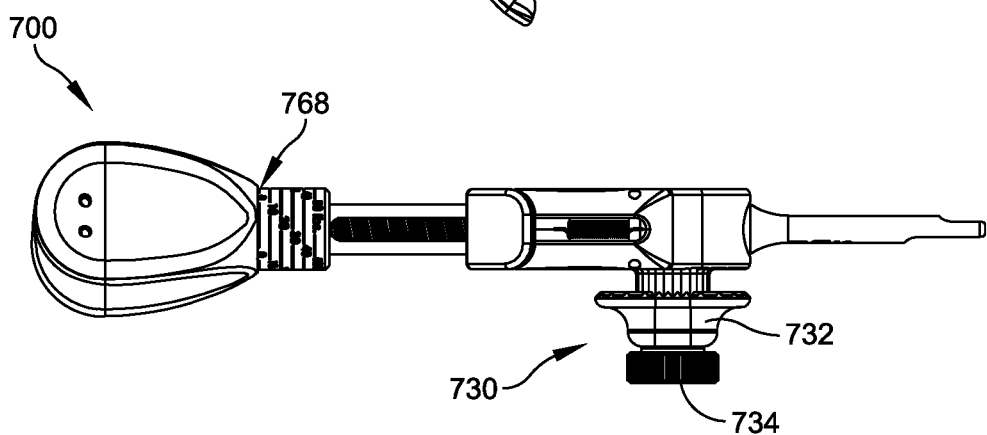
FIG. 13 illustrates a side view of the tension instrument of FIG. 12.
Figure 14:
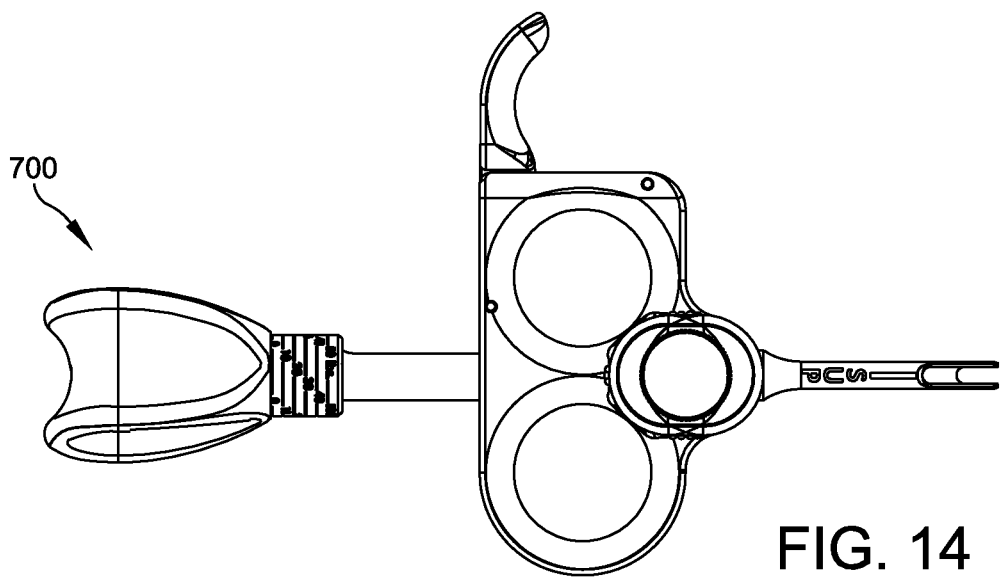
FIG. 14 illustrates a bottom view of the tension instrument of FIG. 12.

FIGS. 12-14 illustrate front, side, and rear views of one embodiment of a tension instrument 700 able to tension a suture or other flexible strand to a known amount of tension force. In this regard, the tension instrument 700 may be used to recreate the tension force applied via the clamp 600, discussed above, before enabling lockout of the suture at the correct tension using a variety of fixation hardware and/or fixation techniques. The disclosed devices may be used in conjunction with a flexible synthetic strand such as, for example, a suture, a suture tape, a cable, or another suitable flexible synthetic strand (hereinafter a "flexible strand," "flexible synthetic strand," or "suture").

In this embodiment, the tension instrument 700 is arranged proximally like the clamp 600 of FIGS. 4-11 with an adjustment mechanism 716 including an inner shaft 718, a hollow outer shaft 720, a trigger 722, a force gauge 724, a handle 726, and a receiver 712, all configured as in the clamp example discussed in relation to FIGS. 4-11 above. In the example of FIGS. 12-14, the outer shaft 706 includes a distal end 711 and a fastener engagement feature 713 at its distal end configured like that of the distal end of the counter-torque anchor driver 570 disclosed in FIGS. 15-18 of U.S. patent application Ser. No. 15/641,592, entitled "EXTRA JOINT STABILIZATION CONSTRUCT" and co-filed with this application on Jul. 5, 2017.

Figure 15:
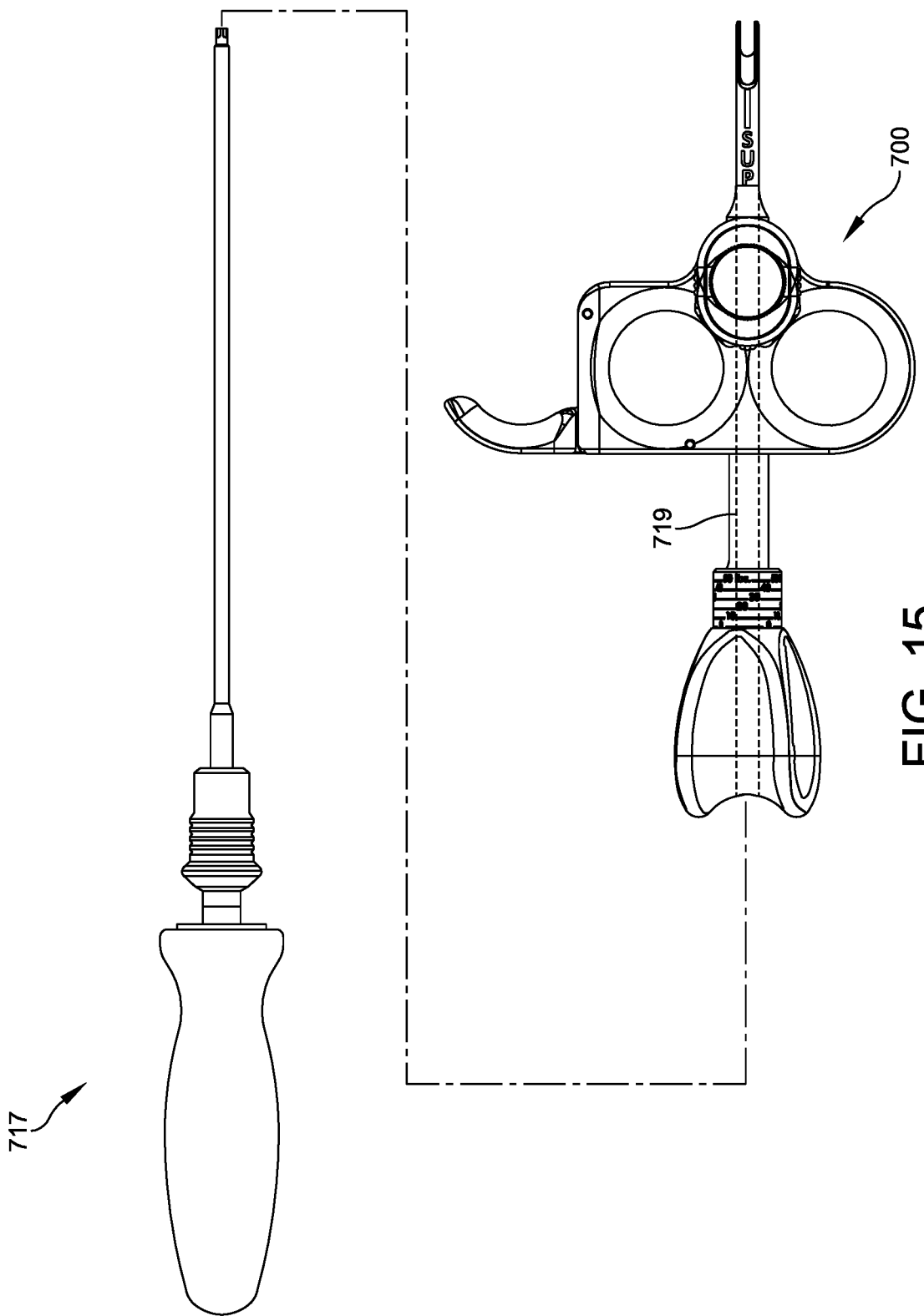
FIG. 15 illustrates an exploded view of the tension instrument of FIG. 12, as cannulated to permit a shaft of a set screw driver to pass through the cannula to insert a set screw into a fixation anchor.

FIG. 15 illustrates that the tension instrument 700 includes a cannula 719 and is cannulated proximally to distally to permit a shaft of a set screw driver 717 and a set screw like, for example, that disclosed in FIGS. 5-7, 12, and/or 15-18 of U.S. patent application Ser. No. 15/641,592, entitled "EXTRA JOINT STABILIZATION CONSTRUCT" and co-filed with this application on Jul. 5, 2017 to pass through the cannula 719 in order to insert the set screw into an anchor like that disclosed in, for example, FIG. 5-7 or 12-14 of U.S. patent application Ser. No. 15/641,592, entitled "EXTRA JOINT STABILIZATION CONSTRUCT" and co-filed with this application on Jul. 5, 2017 that is attached to the tension instrument 700.

In the example of FIGS. 12-14, the receiver 712 of the tension instrument 700 includes a flexible strand clamp 730 or suture clamp 730 (referred hereinbelow as suture clamp 730) including a moveable jaw 732 and a thumb screw 734. A suture may be placed between the receiver 712 and the moveable jaw 732 and clamped in place by tightening the thumb screw 734. With the distal end of the tension instrument engaging or leveraging off of adjacent member such as a bone, anchor, or another member through which a suture passes, and with the suture secured in the suture clamp 730, the receiver 712 may be moved proximally relative to the inner shaft 718. As tension increases in the suture, the outer shaft 720 and the force gauge 724 are forced distally relative to the inner shaft 718, causing the handle 726 to move over the force gauge 724 against the force spring (not shown). The tension in the suture may be read on the force gauge relative to the edge 768 of the handle. The tension instrument 700 may be used in conjunction with an interference screw, anchor, or any other appropriate fixation hardware to recreate the correct tension force and lock the suture in place.

The exemplary instruments of FIGS. 4-15, as well as the exemplary anchors disclosed in U.S. patent application Ser. No. 15/641,592, entitled "EXTRA JOINT STABILIZATION CONSTRUCT" and Ser. No. 15/641,573, entitled "INTRA JOINT STABILIZATION CONSTRUCT" both co-filed with this application on Jul. 5, 2017, may be used to form ligament reinforcement constructs. By way of general explanation, a first suture anchor may be positioned at a first ligament attachment point on a bone. A suture may be routed from the first suture anchor to a second, locking suture anchor at a second ligament attachment point on a bone. The suture may be tensioned to provide a desired level of reinforcement of the ligament and then locked with the second suture anchor. Ligament reinforcing constructs may be provided for any ligament of the skeletal system. For example, various ligament reinforcement constructs will be illustrated for the human ankle. In one example, an anchor is placed in the proximity of the origin of a ligament and a second anchor is placed in the proximity of the insertion of the ligament. One anchor may be any ordinary suture returning anchor, and the second anchor may be a knotless suture locking anchor. The ligament may also undergo a direct repair, e.g., mid substance suturing. In examples of the ankle, the ligaments may include the AITFL, PITFL, ATFL, PTFL, the deep and superficial ligaments of the deltoid complex, and/or any other ligament in need of reinforcement.

Figure 3:
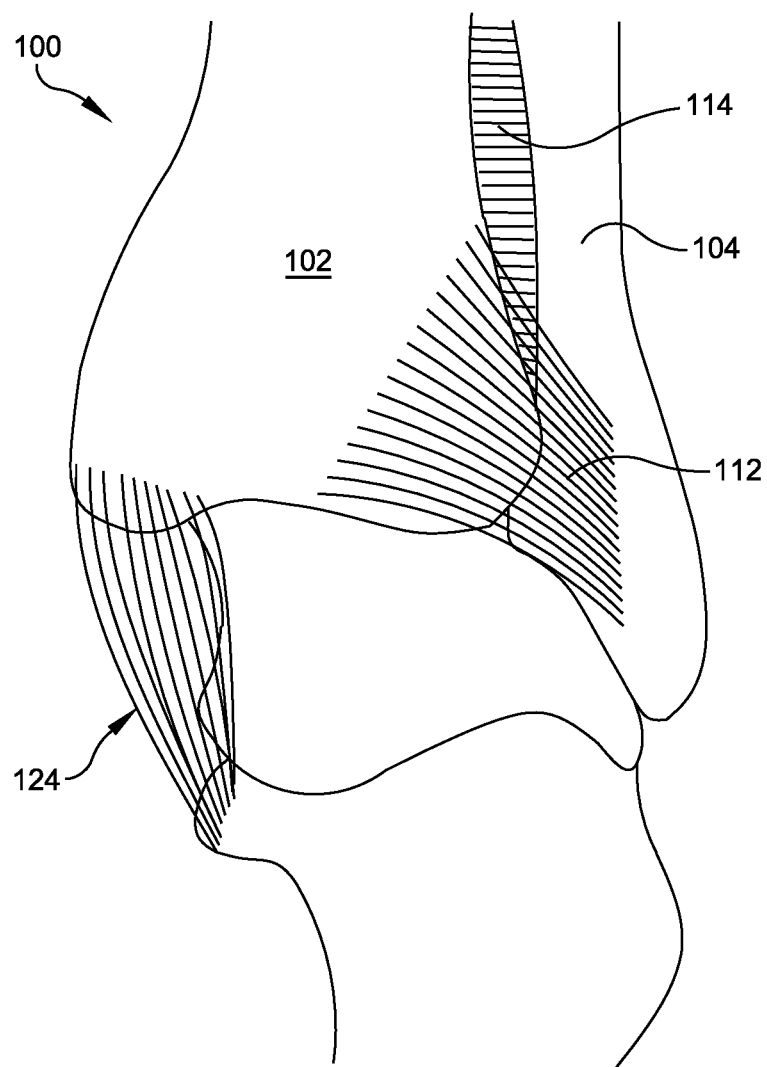
FIG. 3 illustrates a rear view of a human ankle joint.
Figure 16:
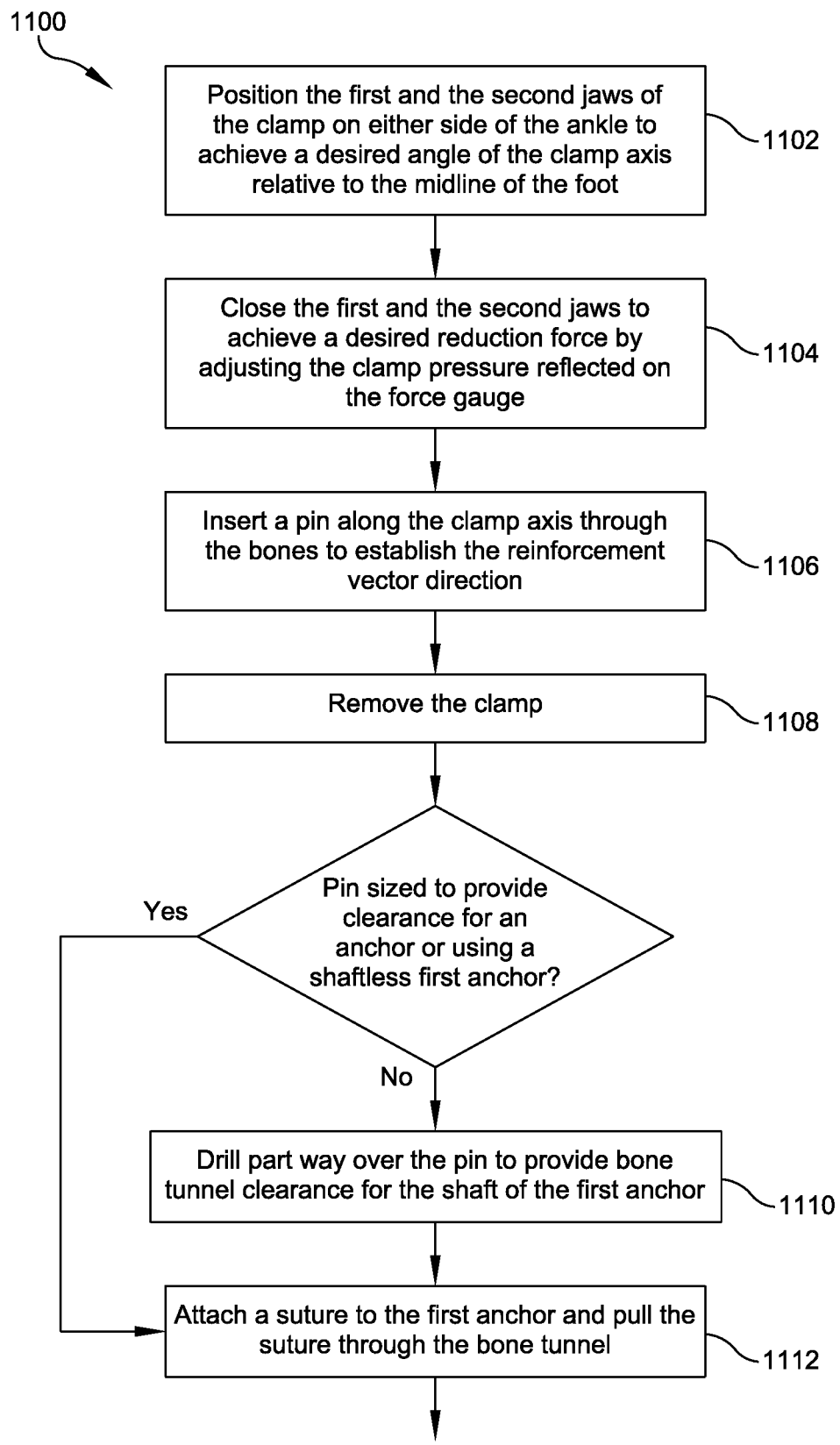
FIG. 16 provides a flowchart detailing an exemplary syndesmosis reinforcement procedure using the clamp instrument of FIG. 4 and the tension instrument of FIG. 12.
Figure 16:
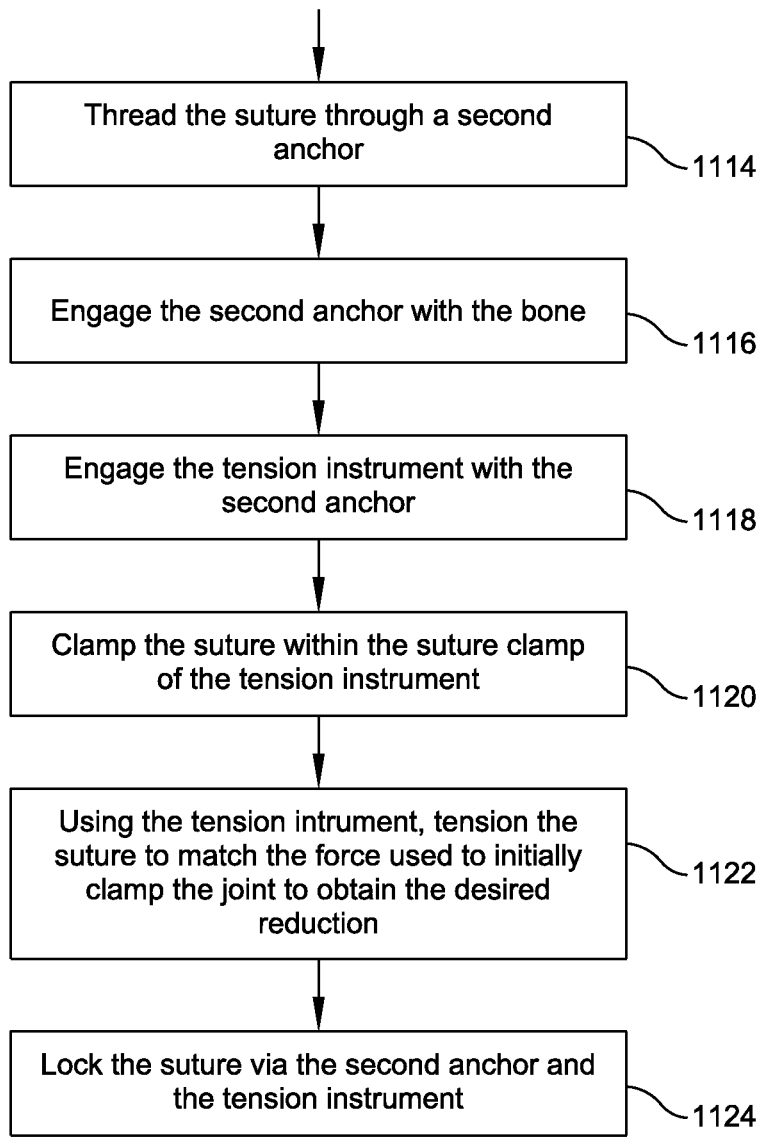

In one example, a reinforcement of the interosseous ligament (IOL) 114 (FIG. 3) may be used to stabilize the ankle syndesmosis. FIG. 16 provides a flowchart detailing the steps of an exemplary syndesmosis reinforcement procedure 1100, while FIGS. 17-21 illustrate the corresponding steps of the exemplary syndesmosis reinforcement procedure. To begin, as shown in FIG. 17, the clamp 600 is positioned such that the v-notch 608a of the first jaw 608 is engaged with the fibula 104 on the lateral side of the ankle, and the point 615 of the second jaw 614 is positioned over the tibia 102 on the medial side of the ankle (FIG. 16, 1102). The angle gauge 680 may be used to set the angle of the clamp axis relative to reference line of the patient's anatomy, e.g., a midline 802 of the foot. For example, it has been found by the present inventors that a force vector of around 30 degrees from perpendicular often provides the best reduction of the fibula relative to the tibia. With the clamp 600 in this initial position, the jaws can be closed to reduce the syndesmosis (FIG. 16, 1104). The ankle can be moved through a range of motion and the reduction evaluated. The reduction force may be increased or decreased by adjusting the clamp pressure and the force direction may be varied by repositioning one or both jaws 608, 614 of the clamp 600 on the bones. The amount of force used to achieve the desired reduction can be read and noted from the force gauge 624.

Once a desired reduction has been achieved, the pin 804 (or a k-wire, etc.) is inserted along the clamp axis 604 through the bones to establish the reinforcement vector direction, as shown in FIG. 10 (FIG. 16, 1106). The clamp may then be removed by rotating the sheath 686 such that the U-shaped groove 688 moves into the open configuration 692 and lifting the clamp from the compression site, as discussed above in relation to FIGS. 8-10 (FIG. 16, 1108). Alternatively, the procedure may continue through the clamp 600.

Figure 18:
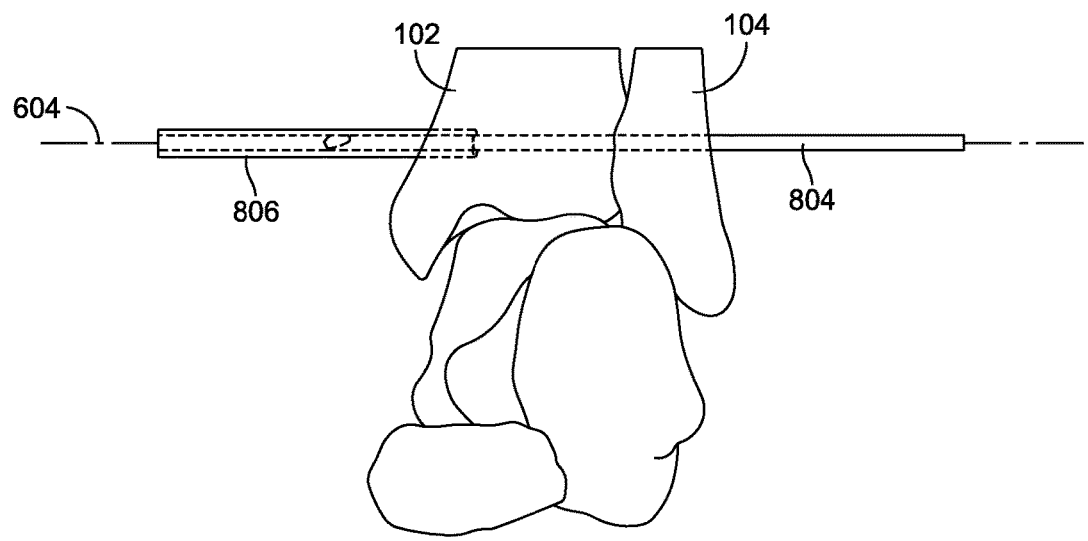
Figure 19:
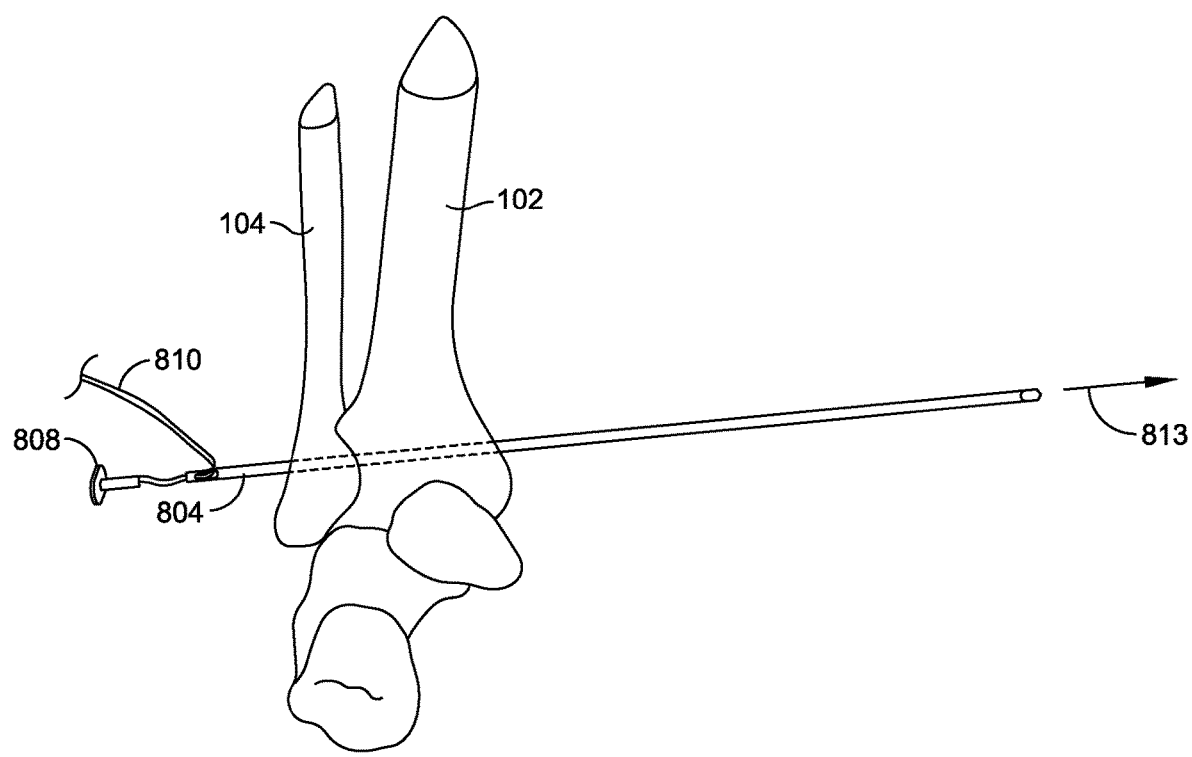
Figures 20, 21:
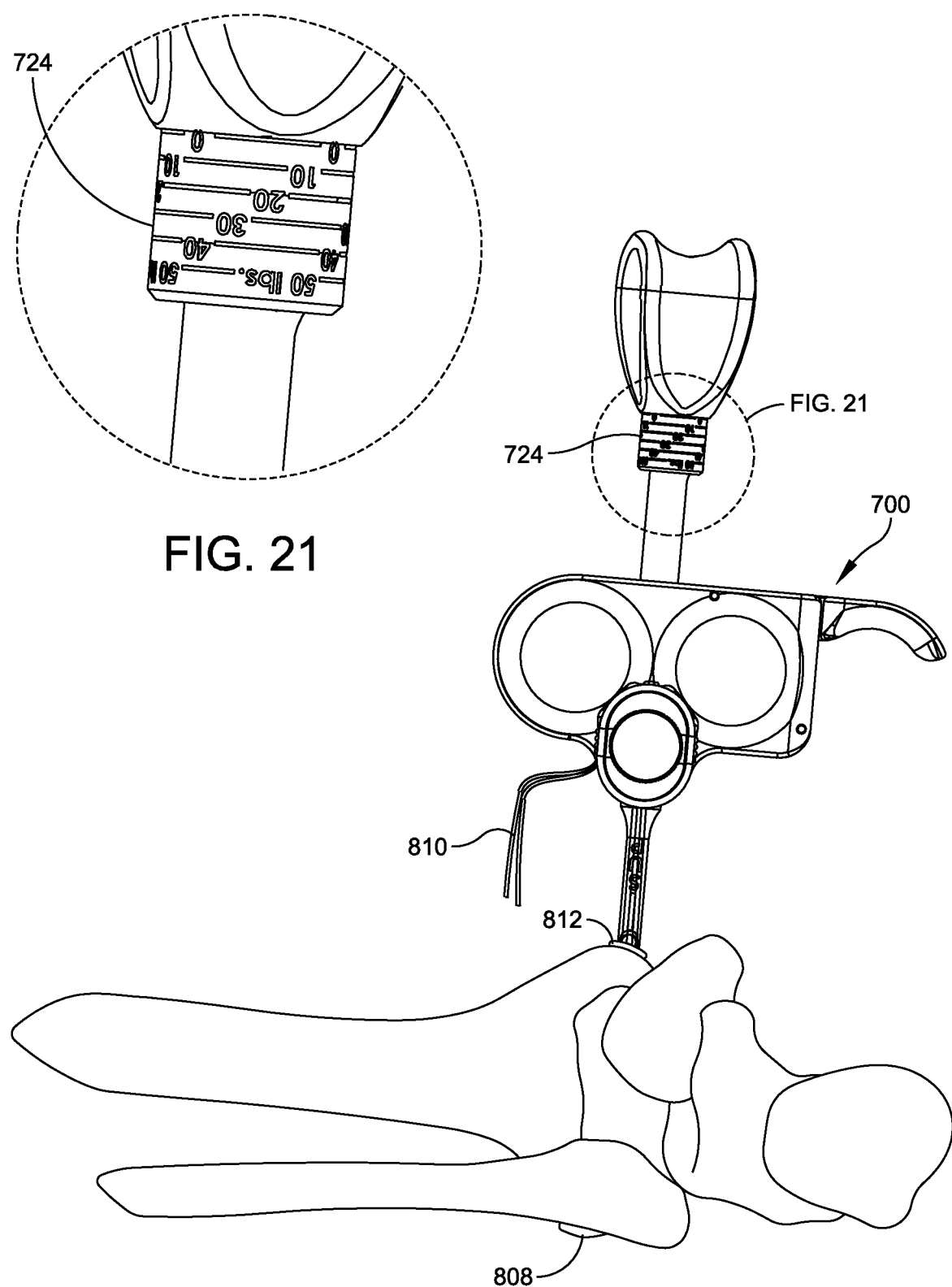

In FIGS. 18-19, the clamp 600 has been removed, and a drill 806 is advanced part-way over the pin 804 to provide clearance for the shaft of a first anchor 808, e.g., anchor 920 disclosed in FIGS. 6-12 of U.S. patent application Ser. No. 15/641,573, entitled "INTRA JOINT STABILIZATION CONSTRUCT," co-filed with this application on Jul. 5, 2017, if necessary as shown in FIG. 18 (FIG. 16, 1110). Alternatively, the pin 804 may be sized to provide the right size hole for the anchor shaft or an anchor without a shaft may be used such as button 200 disclosed in FIG. 4 of U.S. patent application Ser. No. 15/641,573, entitled "INTRA JOINT STABILIZATION CONSTRUCT" co-filed with this application on Jul. 5, 2017. A suture 810 is attached to the first anchor 808 and pulled through the bone tunnel, e.g., by threading the suture 810 through an eye in the pin 804 and pulling the pin and the suture through the bones in the direction of arrow 813, as shown in FIG. 19 (FIG. 16, 1112). The suture is next threaded through a second anchor 812 such as, for example, anchor 300 disclosed in FIGS. 13-19 of U.S. patent application Ser. No. 15/641,573, entitled "INTRA JOINT STABILIZATION CONSTRUCT" co-filed with this application on Jul. 5, 2017 (FIG. 16, 1114). Then the second anchor 812 is engaged with the bone (FIG. 16, 1116), the tension instrument 700 is engaged with the second anchor 812 (FIG. 16, 1118), and the suture is clamped within the suture clamp 730 of the tension instrument 700, as shown in FIG. 20 (FIG. 16, 1120). Tension is applied to the suture to match the force used to clamp the joint and obtain the desired reduction (FIG. 16, 1122) and the suture is knotlessly locked (FIG. 16, 1124), as shown in FIGS. 20-21. In this manner, the directional force vector determined/set during the reduction with the clamp 600 is reproduced precisely, both in direction and force amplitude, by the suture construct.

Figure 22:
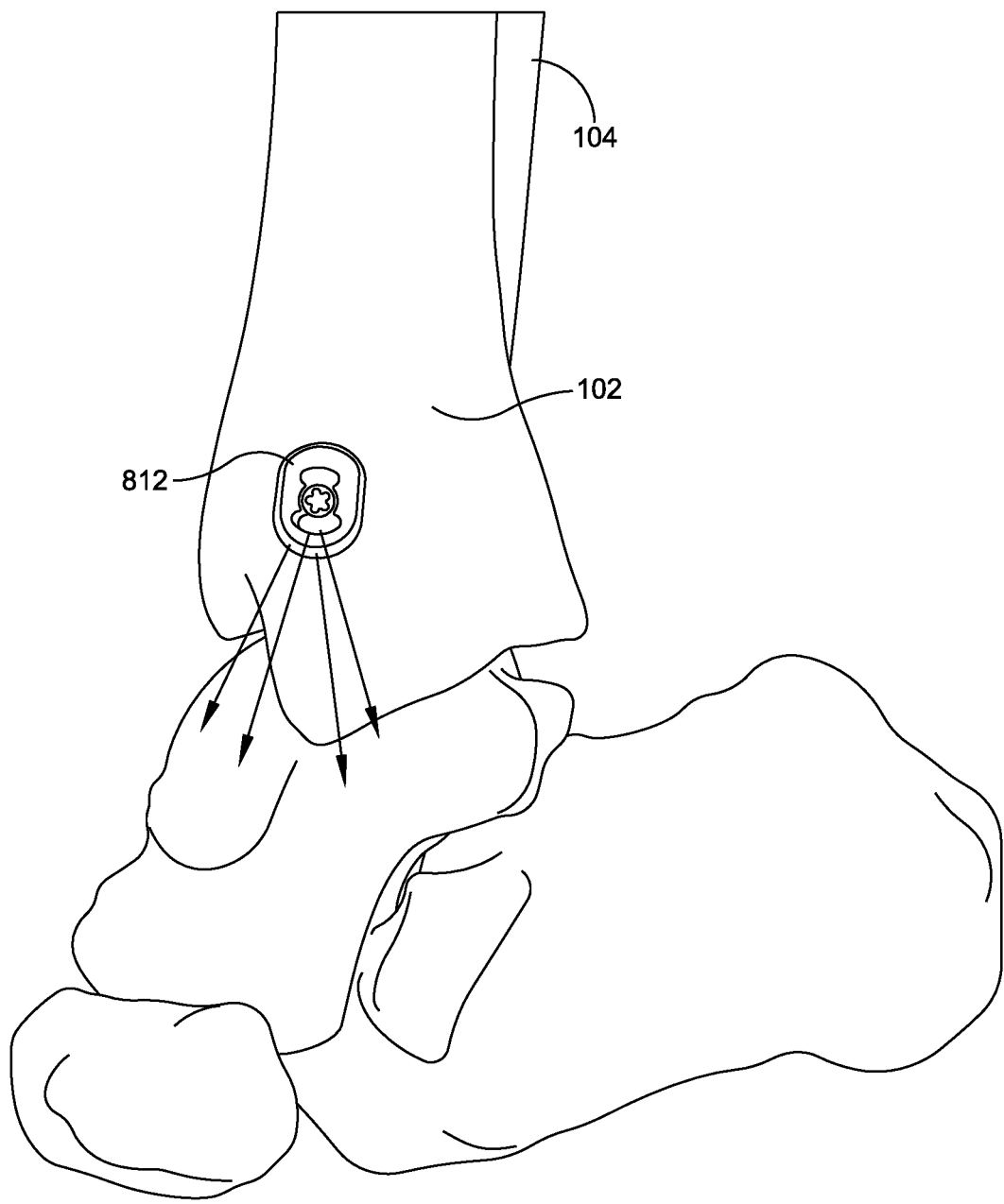
FIG. 22 illustrates a number of supplemental flexible strands attached to a locking anchor used in the syndesmosis reinforcement procedure described and illustrated in FIGS. 16-21.
Figure 23:
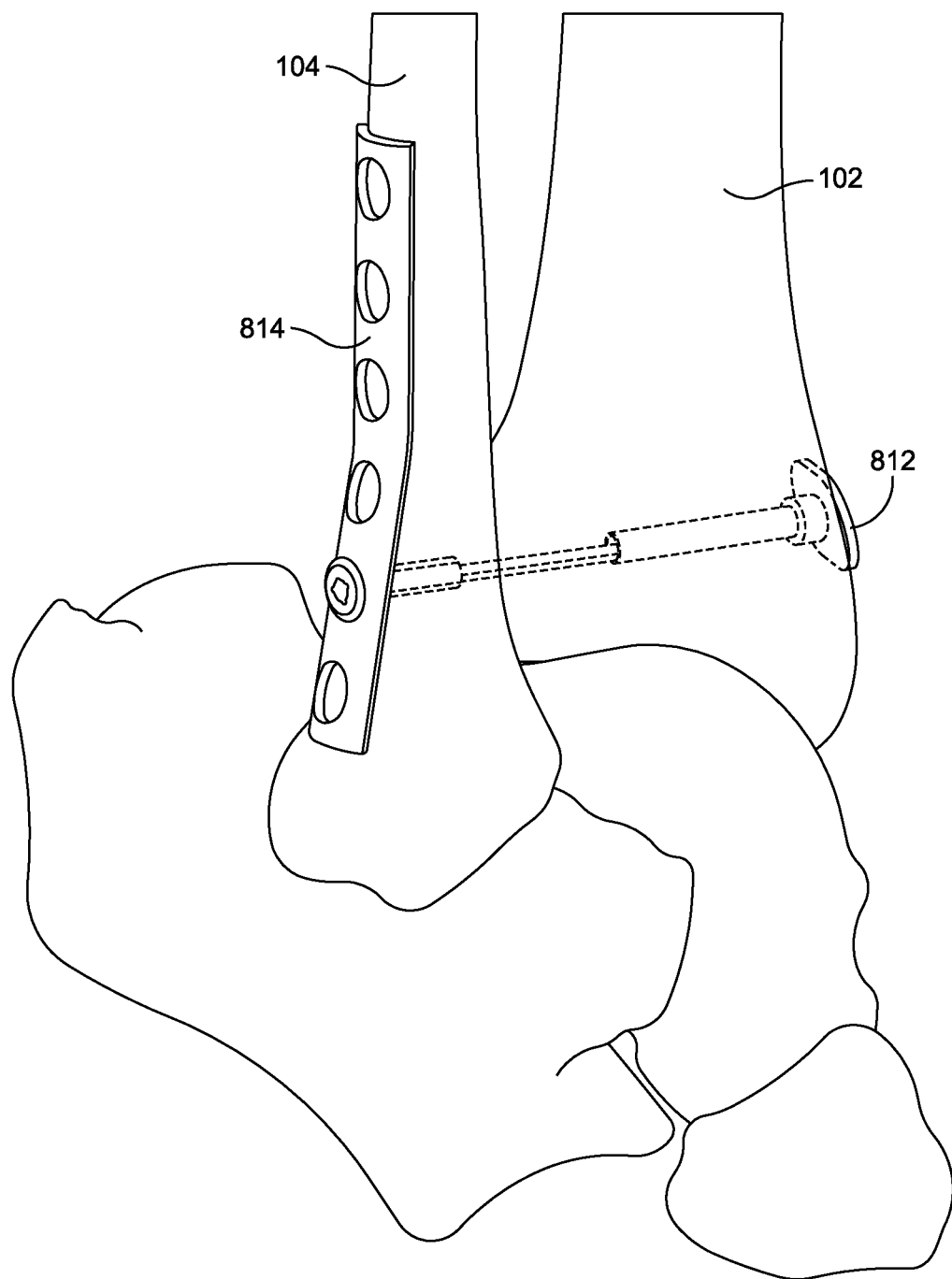
FIG. 23 illustrates a bone plate substituted for a first anchor used in the syndesmosis reinforcement procedure described and illustrated in FIGS. 16-21.

If desired, the ends of the suture coming from the second locking anchor 812 may be trimmed. Alternatively, they may be used to tie to other bones or soft tissues. Likewise, if desired, supplemental sutures may be attached to one or both anchors and used to further reinforce the joint or adjacent joints and soft tissue, as shown in FIG. 22. As shown in FIG. 23, the exemplary reinforcement construct may also be used in conjunction with a bone plate 814.

Notably, while the syndesmosis reinforcement procedure 1100 is described above in relation to reinforcement of the interosseous ligament (IOL) 114 (FIG. 3) between the tibia and fibula, the method could be used to form ligament reinforcement constructs that compress any two bones together to reduce the space between bones and/or to reinforce a ligament across a bone joint to achieve optimal anatomic positioning in both directional alignment and the reduction force applied by the construct.

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. A tension instrument for tensioning and knotlessly locking a flexible strand having first and second opposing flexible strand ends, the first flexible strand end fixed adjacent to a first member and the second flexible strand end free proximal to the first member and adjacent to a second member, the tension instrument comprising:

a member engagement feature configured to engage with the second member through which the second flexible strand end passes; and an adjustment mechanism operably coupled to a proximal end of the member engagement feature, the adjustment mechanism including:

a selectively adjustable flexible strand clamp configured to capture the second flexible strand end and translate the second flexible strand end proximally relative to the member engagement feature to place a tensile force on the flexible strand between the first and the second members;

a force gauge operably coupled with the selectively adjustable flexible strand clamp, the force gauge including force indicia to provide an indication of the tensile force placed on the flexible strand; and a pathway extending through the adjustment mechanism from a proximal end to a distal end adjacent the member engagement feature to provide clearance for fixation hardware that knotlessly locks the second flexible strand end relative to the second member to maintain the tensile force between the first and the second flexible strand ends.

2. The tension instrument of claim 1, wherein the adjustment mechanism includes a gross adjustment control and a fine adjustment control.

3. The tension instrument of claim 1, wherein the clamp includes finger grips and a thumb grip configured to enable one-handed operation to apply compression force.

4. The tension instrument of claim 1, wherein the clamp includes a release trigger configured to release compression force.

5. The tension instrument of claim 4, wherein the release trigger is configured to enable one-handed operation for both application of compression force and release of compression force.

6. The tension instrument of claim 1, wherein at least one of the first and the second members comprises a bone portion.

7. The tension instrument of claim 1, wherein at least one of the first and the second members comprises a flexible strand fixation anchor.

8. The tension instrument of claim 7, wherein the member engagement feature comprises a fastener engagement feature configured to engage with the flexible strand fixation anchor.

9. The tension instrument of claim 7, wherein the fastener engagement feature comprises a pair of counter-torque prongs.

10. The tension instrument of claim 1, wherein the pathway extending through the adjustment mechanism is a cannula.

11. The tension instrument of claim 1, wherein the tensile force between the first and the second flexible strand ends is placed only upon the flexible strand.

12. The tension instrument of claim 1, wherein the adjustment mechanism further comprises:

a handle disposed about the force gauge, the handle having a proximal end and a distal end;

an outer shaft extending proximally to distally between the force gauge and the member engagement feature;

an inner shaft disposed within the outer shaft, the inner shaft extending proximally to distally between the proximal end of the handle and the member engagement feature;

a force spring disposed about the inner shaft in a space between the inner shaft and the force gauge, the force spring extending proximally to distally between the proximal end of the handle and the outer shaft, wherein an amount of force required to compress the force spring is proportional to a distance the force spring is compressed;

a receiver mounted upon the selectively adjustable flexible strand clamp, the receiver slidably coupled with the inner shaft, wherein:

when the member engagement feature is engaged with the second member and the second flexible strand end is secured within the selectively adjustable flexible strand clamp, translating the receiver proximally relative to the inner shaft forces the outer shaft and the force gauge distally relative to the inner shaft, thereby causing the handle to move proximally over the force gauge against the force spring and compressing the force spring such that the distal end of the handle aligns with one of the force indicia indicating the tensile force placed on the flexible strand.

\* \* \* \* \*